US011083461B2

(12) United States Patent
Lee et al.

(10) Patent No.: US 11,083,461 B2
(45) Date of Patent: Aug. 10, 2021

(54) SURGICAL STAPLING APPARATUS WITH REUSABLE COMPONENTS

(71) Applicant: Covidien LP, Mansfield, MA (US)

(72) Inventors: Kin Ying Lee, Singapore (SG); Hui Zhan, Shanghai (CN); Feng Wang, Shanghai (CN)

(73) Assignee: Covidien LP, Mansfield, MA (US)

( * ) Notice: Subject to any disclaimer, the term of this patent is extended or adjusted under 35 U.S.C. 154(b) by 103 days.

(21) Appl. No.: 16/246,826

(22) Filed: Jan. 14, 2019

(65) Prior Publication Data

US 2019/0142427 A1    May 16, 2019

Related U.S. Application Data

(63) Continuation of application No. 14/759,948, filed as application No. PCT/CN2014/073447 on Mar. 14, 2014, now Pat. No. 10,178,994.

(30) Foreign Application Priority Data

Mar. 15, 2013   (CN) .......................... 201310175344.1

(51) Int. Cl.
*A61B 17/068* (2006.01)
*A61B 17/115* (2006.01)
(Continued)

(52) U.S. Cl.
CPC ... *A61B 17/1155* (2013.01); *A61B 2017/0046* (2013.01); *A61B 2017/00314* (2013.01);
(Continued)

(58) Field of Classification Search
CPC ...... A61B 2017/003; A61B 2017/0069; A61B 2017/2902; A61B 2017/2901; A61B 2017/2919; A61B 2017/2912
See application file for complete search history.

(56) References Cited

U.S. PATENT DOCUMENTS 3,177,683 A * 4/1965 Olson ...................... F16C 1/00
                                                    464/151
3,193,165 A   7/1965 Akhalaya et al.
(Continued)

FOREIGN PATENT DOCUMENTS

| CA | 908529 A | 8/1972 |
| CA | 2604982 A1 | 4/2008 |

(Continued)

OTHER PUBLICATIONS

Examination Report No. 1 issued in corresponding Australian application No. 2014231439 dated Jan. 30, 2018, 4 pages.
(Continued)

*Primary Examiner* — Andrew M Tecco
*Assistant Examiner* — Eyamindae C Jallow

(57) ABSTRACT

A surgical stapling apparatus includes a handle, an elongated body, a firing assembly, and a stapling assembly. The body extends from the handle and includes an engagement member rotatably supported on to a distal portion of the body. The engagement member defines an engagement slot and is axially movable about the body from a retracted position to an advanced position. The firing assembly includes a trigger, firing link, and pusher link. The pusher link is movably supported for distal translation through the body in response to actuation of the trigger. The stapling assembly houses a plurality of surgical staples and includes an outer shell having an engagement tab. The engagement member is rotatable relative to the body and the stapling assembly to releasably position the engagement tab within the engagement slot, thereby securing the stapling assembly at the distal end of the body.

17 Claims, 31 Drawing Sheets

(51) Int. Cl.
*A61B 17/00* (2006.01)
*A61B 90/00* (2016.01)

(52) U.S. Cl.
CPC .............. *A61B 2017/00323* (2013.01); *A61B 2017/00473* (2013.01); *A61B 2090/0811* (2016.02); *A61B 2090/0813* (2016.02)

(56) References Cited

U.S. PATENT DOCUMENTS

| | | |
|---|---|---|
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A * | 9/1994 | Blanco ................ A61B 17/115 227/19 |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |

(56) References Cited

U.S. PATENT DOCUMENTS

| | | |
|---|---|---|
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 * | 1/2007 | Milliman ............ A61B 17/1114 227/175.1 |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 * | 8/2010 | Ortiz ................ A61B 17/00234 227/175.1 |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |

(56) References Cited

U.S. PATENT DOCUMENTS

| | | |
|---|---|---|
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,317,075 B2 | 11/2012 | Milliman |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,463,022 B2 * | 10/2016 | Swayze ............ A61B 17/1155 |
| 10,178,994 B2 | 1/2019 | Lee et al. |
| 2003/0111507 A1 | 6/2003 | Nunez |
| 2005/0023325 A1 * | 2/2005 | Gresham ............ A61B 17/115 |
| | | 227/176.1 |
| 2005/0051597 A1 | 3/2005 | Toledano |
| 2005/0107813 A1 | 5/2005 | Gilete Garcia |
| 2005/0116009 A1 * | 6/2005 | Milliman ............ A61B 17/072 |
| | | 227/176.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 * | 3/2007 | Roby ............... A61B 17/32053 |
| | | 606/219 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0076451 A1 * | 3/2010 | Zwolinski ............ A61B 1/005 |
| | | 606/113 |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0237132 A1 | 9/2010 | Measamer et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0001916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |

(56) References Cited

U.S. PATENT DOCUMENTS

| | | |
|---|---|---|
| 2011/0192882 A1 | 8/2011 | Hess et al. |
| 2012/0123457 A1 | 5/2012 | Milliman et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0115014 A1 | 4/2015 | Matonick et al. |
| 2015/0122869 A1 | 5/2015 | Aronhalt et al. |
| 2015/0129635 A1 | 5/2015 | Williams et al. |
| 2015/0129636 A1 | 5/2015 | Mulreed |
| 2016/0143641 A1 | 5/2016 | Sapienza |
| 2016/0192938 A1 | 7/2016 | Sgroi, Jr. |

FOREIGN PATENT DOCUMENTS

| | | | |
|---|---|---|---|
| CA | 2717990 A1 | 4/2011 | |
| CN | 1742684 A | 3/2006 | |
| CN | 102652001 A | 8/2012 | |
| DE | 1057729 B | 5/1959 | |
| DE | 3301713 A1 | 7/1984 | |
| EP | 0152382 A2 | 8/1985 | |
| EP | 0173451 A1 | 3/1986 | |
| EP | 0190022 A2 | 8/1986 | |
| EP | 0282157 A1 | 9/1988 | |
| EP | 0503689 A2 | 9/1992 | |
| EP | 1354560 A2 | 10/2003 | |
| EP | 2505148 A1 | 10/2012 | |
| EP | 2524656 A2 | 11/2012 | |
| EP | 2674117 A1 * | 12/2013 | ............ A61B 17/29 |
| FR | 1136020 A | 5/1957 | |
| FR | 1461464 A | 2/1966 | |
| FR | 1588250 A | 4/1970 | |
| FR | 2443239 A1 | 7/1980 | |
| GB | 1185292 A | 3/1970 | |
| GB | 2016991 A | 9/1979 | |
| GB | 2038692 A | 7/1980 | |
| GB | 2070499 A | 9/1981 | |
| JP | 2004524121 A | 8/2004 | |
| JP | 5757135 B2 | 7/2015 | |
| NL | 7711347 A | 4/1979 | |
| SU | 1509052 A1 | 9/1989 | |
| WO | 8706448 A1 | 11/1987 | |
| WO | 8900406 A1 | 1/1989 | |
| WO | 9006085 A1 | 6/1990 | |
| WO | 0154594 A1 | 8/2001 | |
| WO | 02080781 A2 | 10/2002 | |
| WO | 2008107918 A1 | 9/2008 | |

OTHER PUBLICATIONS

First Chinese office action issued in corresponding application No. 201310175344.1 dated Mar. 20, 2017.

Japanese Office Action issued in corresponding Japanese application No. 2015-561929 dated Nov. 24, 2017.

European search report issued in corresponding application No. 14765246.5 dated Oct. 20, 2016.

Second Chinese office action issued in corresponding application No. 201310175344.1 dated Nov. 15, 2017.

International Search Report for PCT/CN2014/073447 date of completion is May 21, 2014 (2 pages).

* cited by examiner

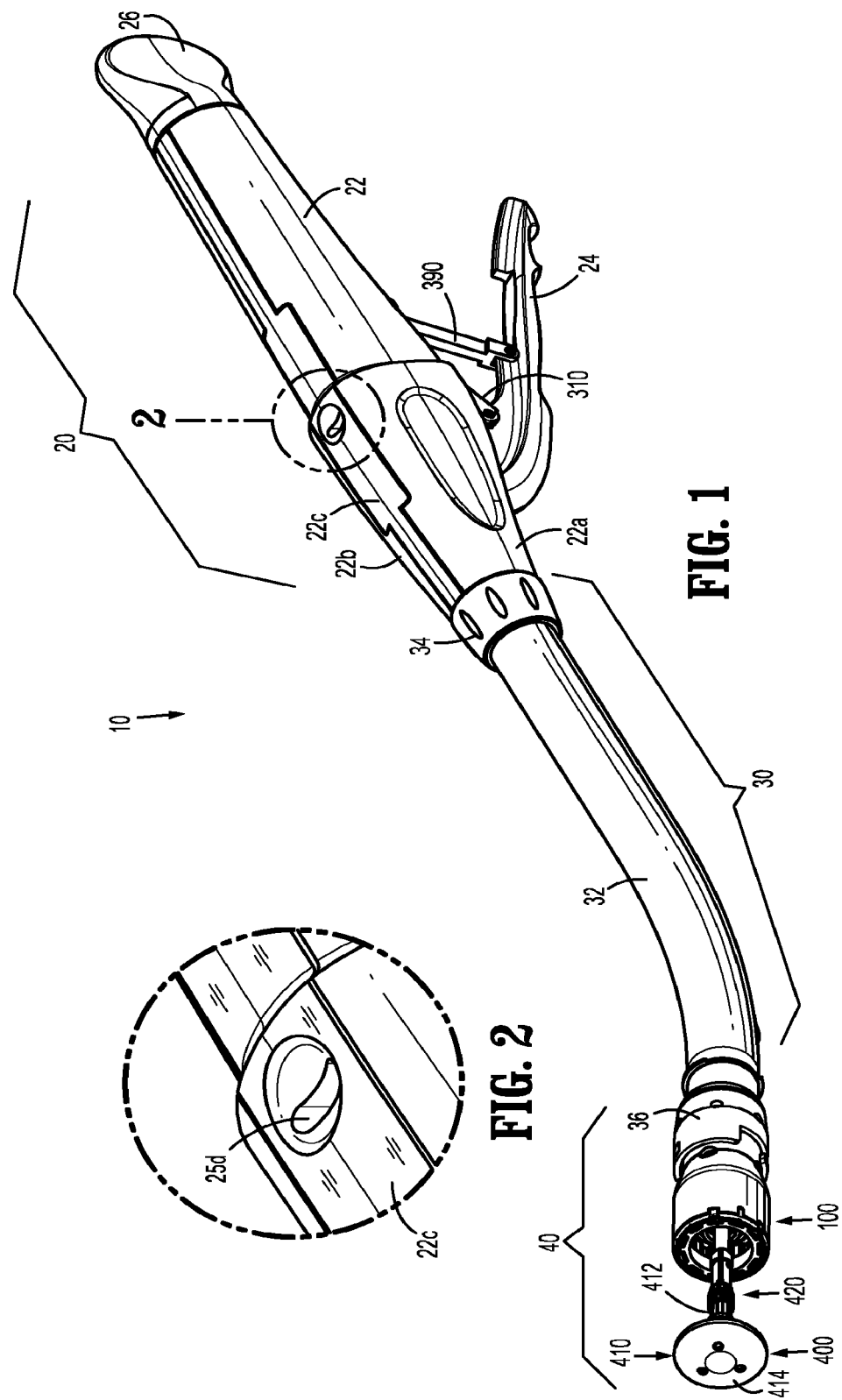

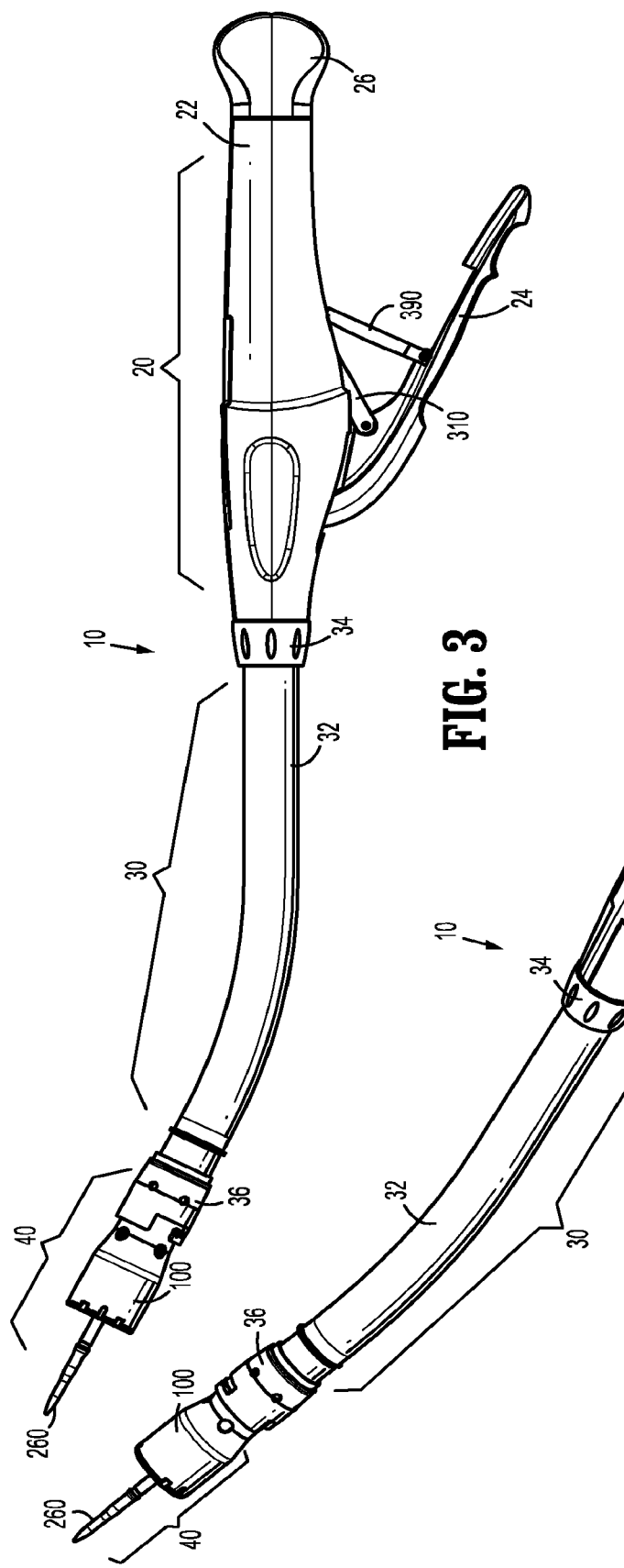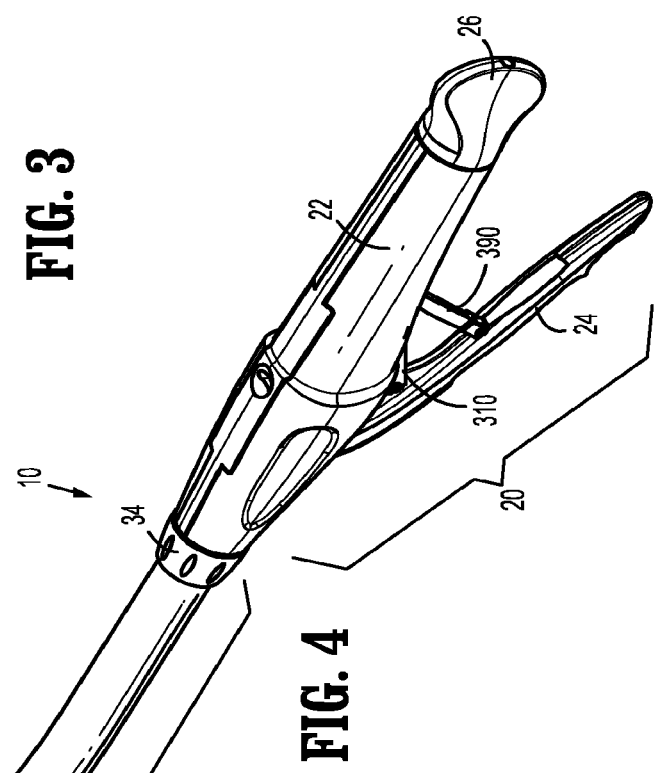
FIG. 3
FIG. 4

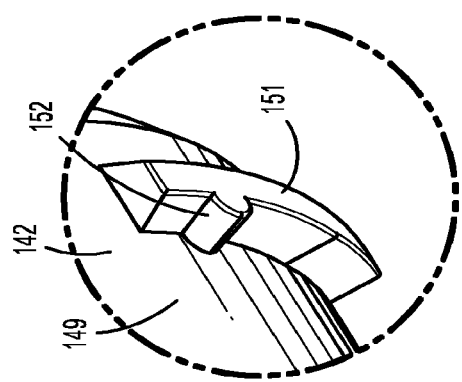
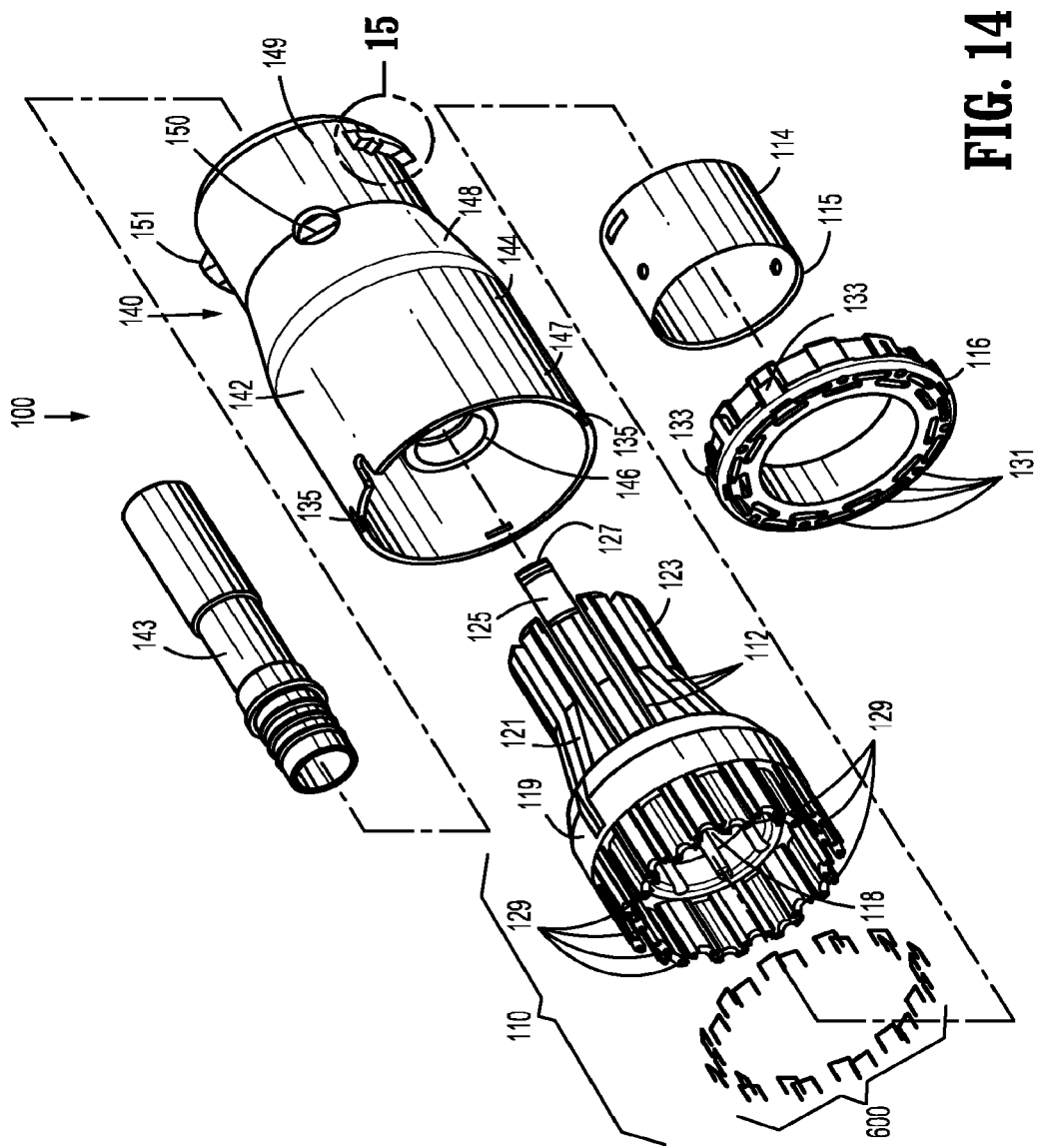

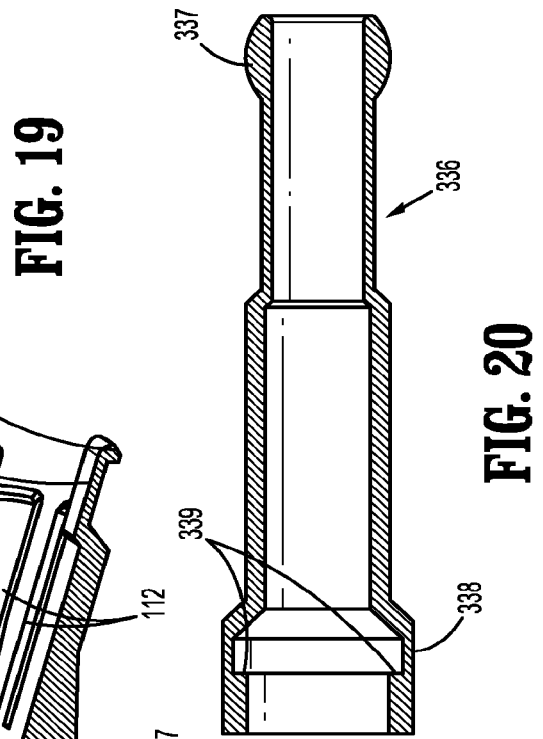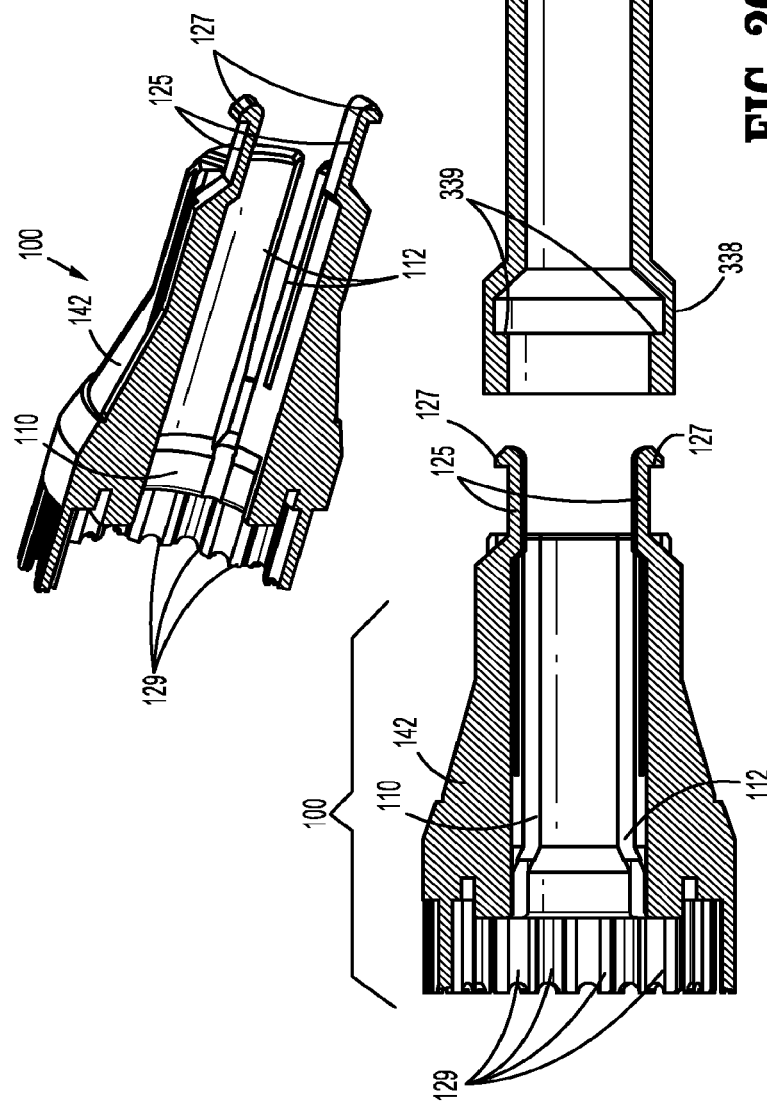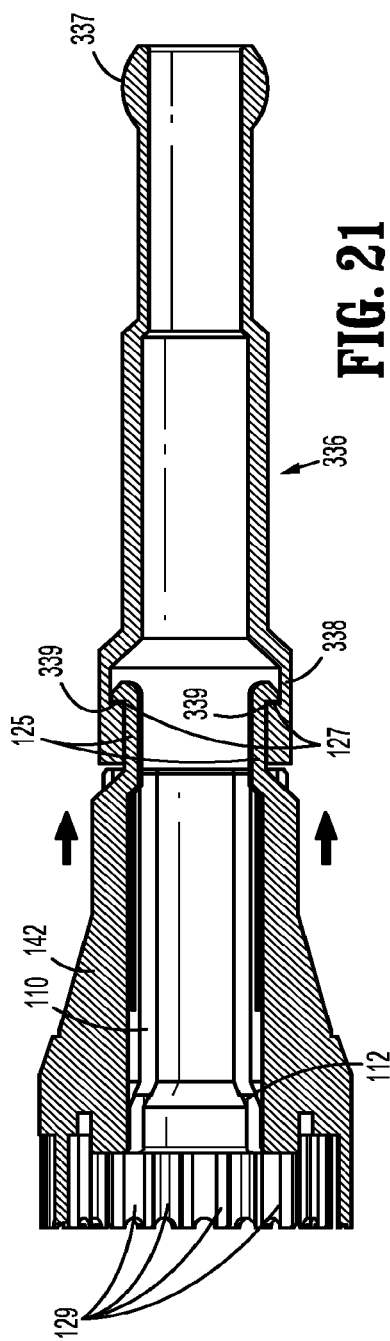

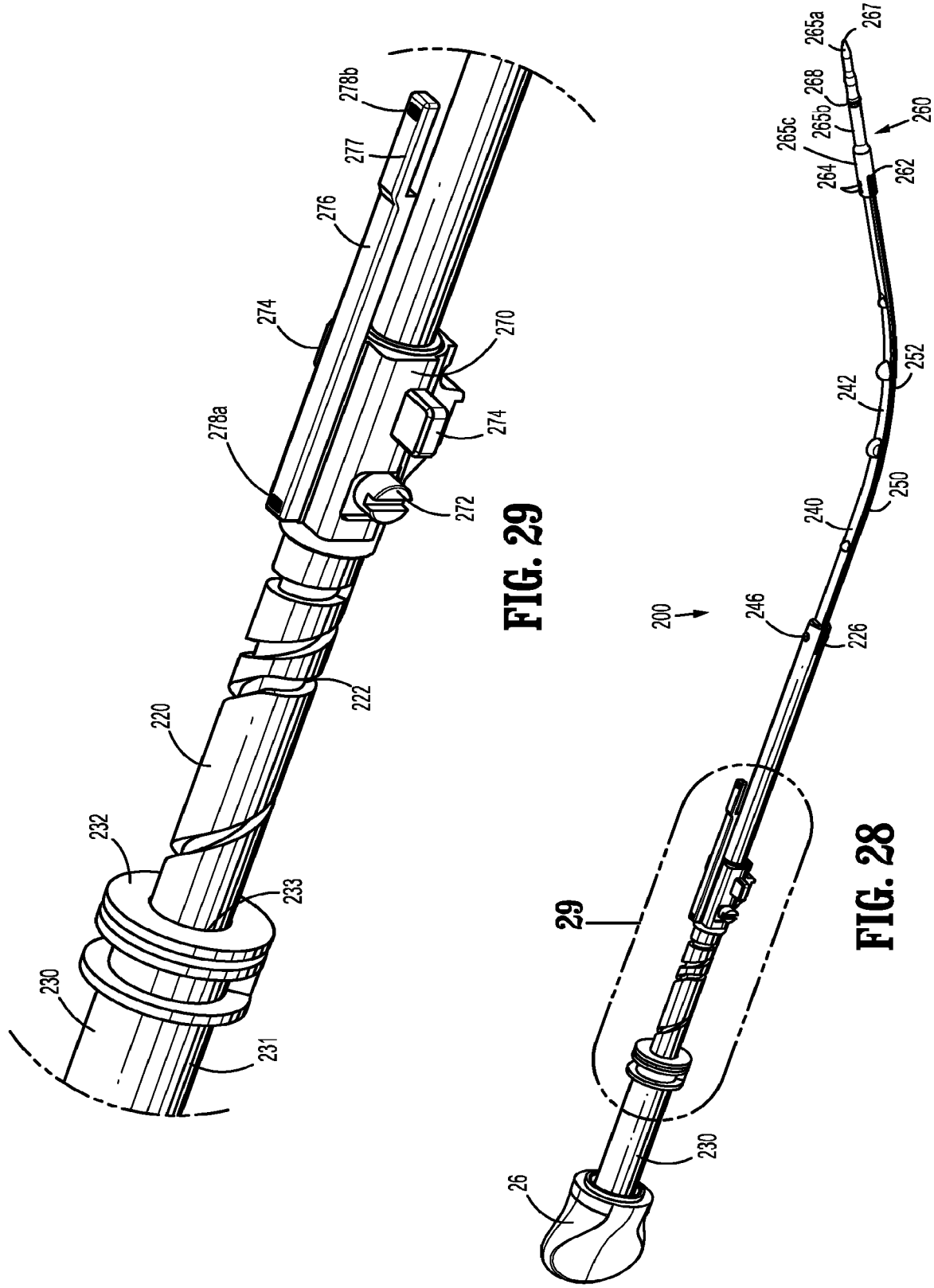

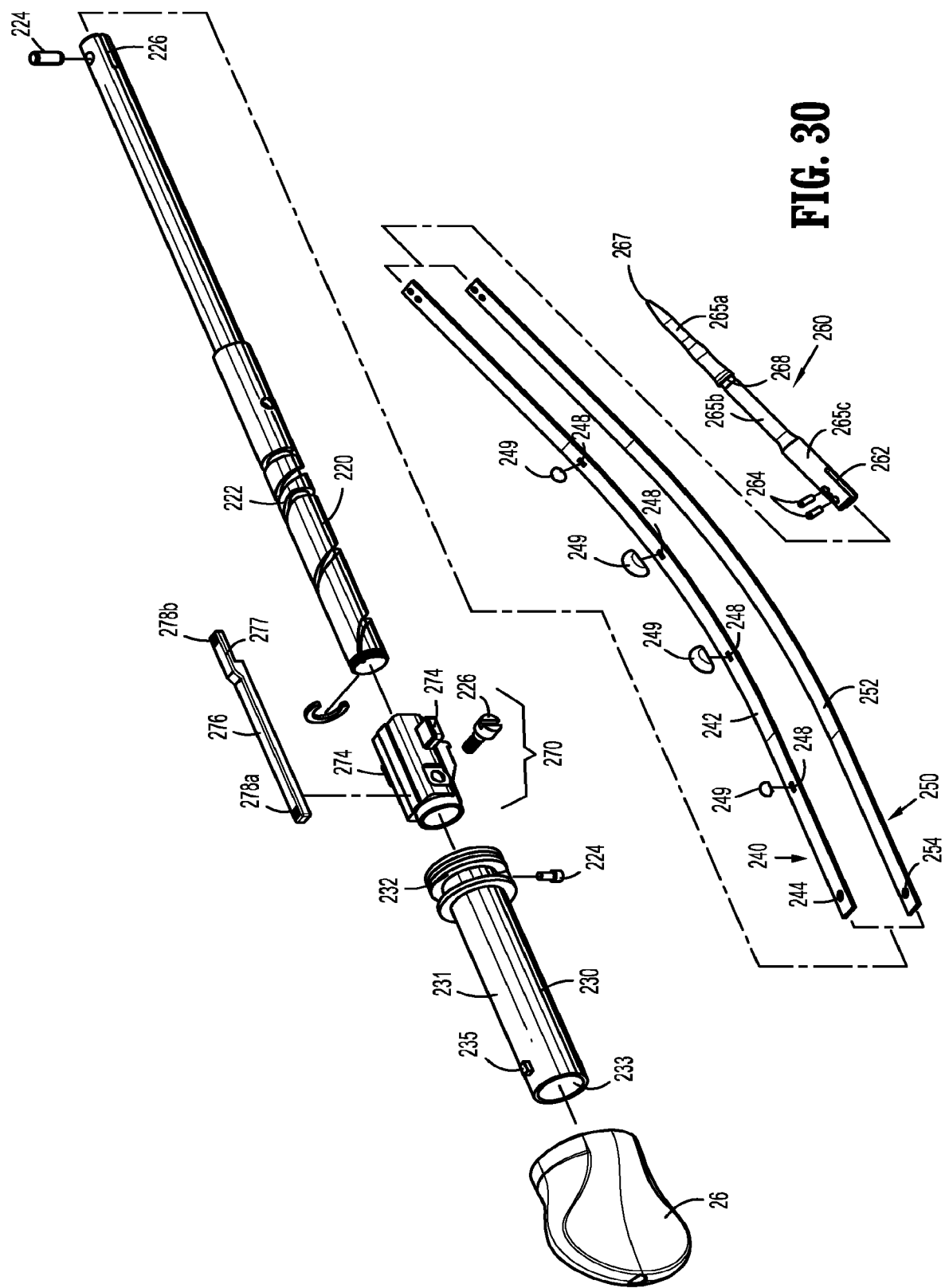

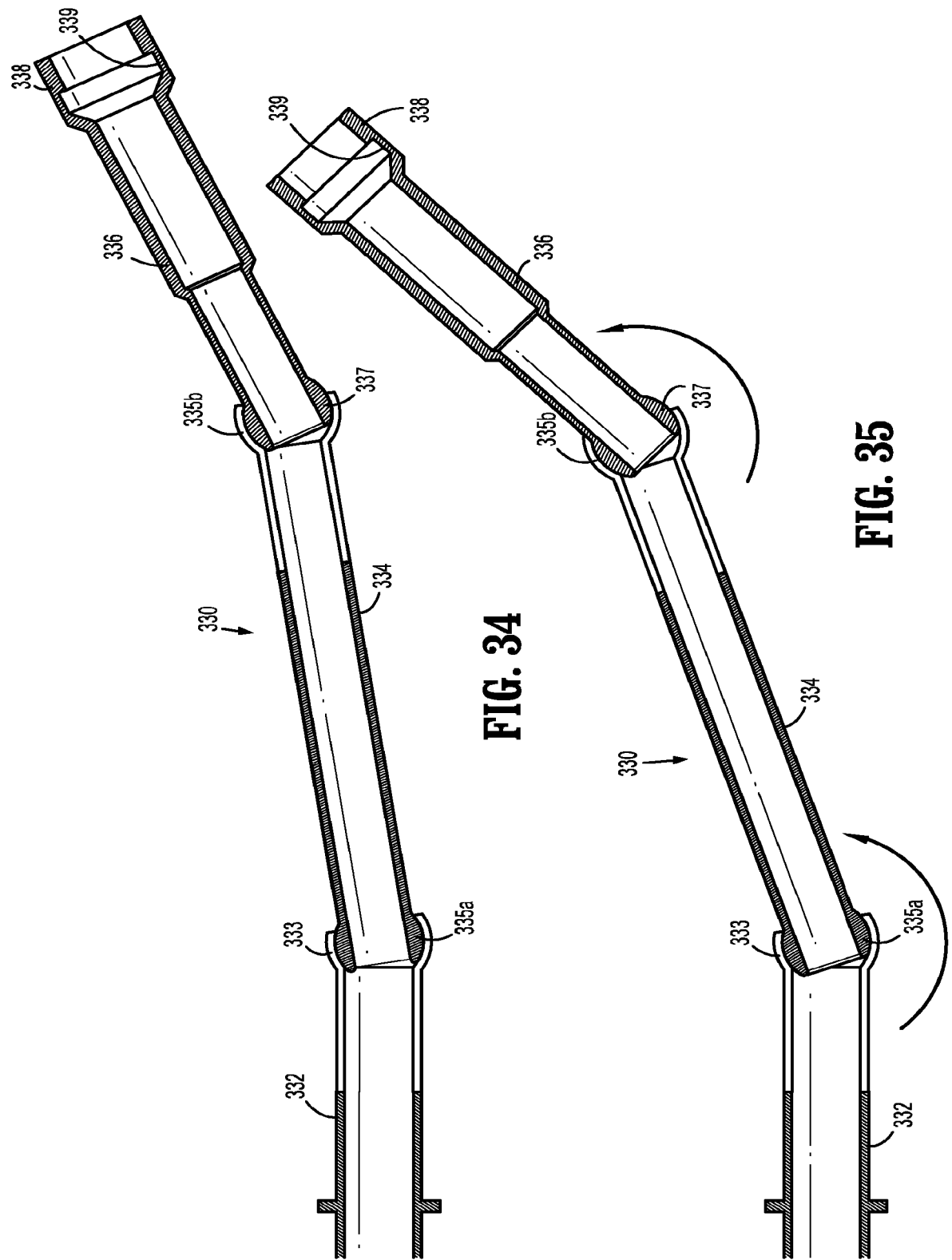

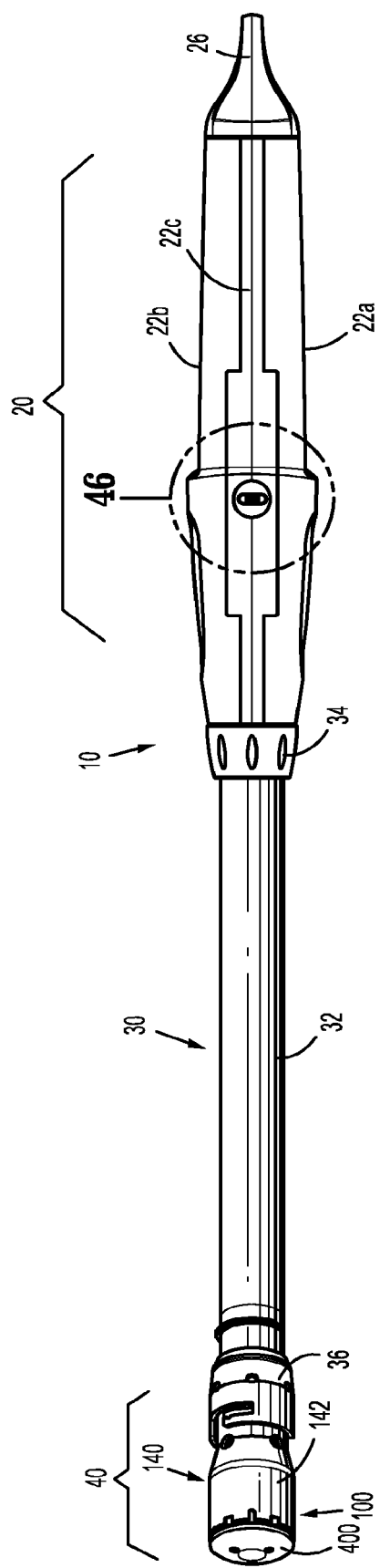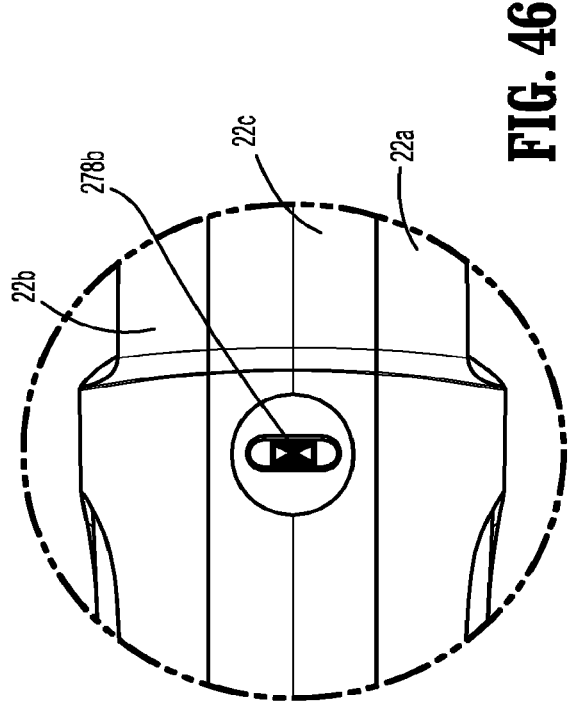
FIG. 45
FIG. 46

SURGICAL STAPLING APPARATUS WITH REUSABLE COMPONENTS

CROSS-REFERENCE TO RELATED APPLICATIONS

This is a continuation of U.S. patent application Ser. No. 14/759,948, filed Jul. 9, 2015, which is a U.S. National Stage Application filed under 35 U.S.C. § 371(a) of International Patent Application Serial No. PCT/CN2014/073447, filed Mar. 14, 2014, which claims the benefit of and priority to Chinese Patent Application Serial No. 201310175344.1, filed Mar. 15, 2013, the entire contents of which are hereby incorporated by reference.

BACKGROUND

Technical Field

The present disclosure relates generally to a surgical stapling apparatus for applying surgical staples to body tissue and, more particularly, to a surgical stapling apparatus for performing circular anastomosis of hollow tissue structures which includes reusable components.

Background of Related Art

Anastomosis refers to the surgical joining of separate hollow tissue sections. Typically, an anastomosis procedure follows surgery in which a diseased or defective section of a hollow tissue structure is removed, thus requiring the joining of the remaining end sections of the tissue structure. Depending on the particular procedure being performed and/or other factors, the end sections of the tissue may be joined by circular anastomosis, e.g., end-to-end anastomosis, end-to-side anastomosis, or side-to-side anastomosis.

In a circular anastomosis procedure, two end sections of a tubular organ are joined using a stapling apparatus that drives a circular array of staples through each of the end sections to join the end sections to one another in end-to-end relation and simultaneously cores any tissue within the newly joined hollow tissue structure to clear the passage defined by the hollow tissue structure. A typical circular anastomosis apparatus includes an elongated shaft having a handle portion at a proximal end and a staple holding component at a distal end. An anvil assembly including an anvil rod and an attached anvil head is mounted to the distal end of the elongated shaft adjacent the staple holding component. In use, the end portions to be joined are clamped between the anvil head and the staple holding component. The clamped end portions are then joined to one another by driving one or more staples from the staple holding component, through the tissue, and into the anvil head to form the staples about the tissue. An example of such a circular anastomosis apparatus is described in U.S. Pat. No. 7,857,187 to Milliman, the entire contents of which is hereby incorporated by reference herein in its entirety.

Typically, surgical stapling apparatus for performing circular anastomosis procedures are disposable after a single use. Because of the high costs associated with the use of disposable surgical stapling apparatus, a need exists for a surgical stapling apparatus that includes reusable components and is configured to facilitate effective sterilization of the reusable components.

SUMMARY

A surgical stapling apparatus provided in accordance with the present disclosure includes a handle portion, an elongated body portion, a firing assembly, and a stapling assembly. The elongated body portion extends distally from the handle portion. The elongated body portion includes an engagement member rotatably supported on a distal portion of the elongated body portion. The engagement member defines an engagement slot and is axially movable about the elongated body portion from a retracted position to an advanced position. The firing assembly includes a firing trigger, a firing link, and a pusher link. The pusher link extends through the elongated body portion and is configured for distal translation through the elongated body portion in response to actuation of the firing trigger. The stapling assembly is configured to house a plurality of surgical staples. The stapling assembly includes an outer shell having an engagement tab. The engagement member is rotatable relative to the elongated body portion and the stapling assembly to releasably engage the engagement tab within the engagement slot to releasably secure the stapling assembly at the distal end of the elongated body portion such that, in response to distal advancement of the firing pusher, the plurality of surgical staples are ejected from the stapling assembly.

In embodiments, the surgical stapling apparatus further includes an approximation assembly. The approximation assembly includes a drive member configured to extend distally from the elongated body portion and the stapling assembly. The distal end of the drive member is configured to releasably engage an anvil assembly.

In embodiments, the surgical stapling apparatus further includes an approximation knob extending from the handle portion. The approximation knob is coupled to the drive member and is selectively actuatable to move the anvil assembly between a spaced-apart position and an approximated position relative to the stapling assembly.

In embodiments, the drive member defines a helical channel and the approximation knob is coupled to a pin disposed within the helical channel such that rotation of the approximation knob effects translation of the drive member.

In embodiments, the handle portion includes an indicator window configured to permit visualization into the handle portion to confirm a position of the anvil assembly relative to the stapling assembly.

In embodiments, a biasing member is disposed about the elongated body portion and configured to bias the engagement member towards the retracted position. As such, the engagement tab is retained in engagement within the engagement slot under the bias of the biasing member.

In embodiments, the engagement tab further includes an engagement nub and the engagement slot further includes an engagement notch. The engagement nub is configured to engage the engagement notch to secure the stapling assembly at the distal end of the elongated body portion.

In embodiments, the stapling assembly includes a cartridge assembly disposed within the outer shell. The cartridge assembly may include a pusher including a plurality of pusher fingers configured to support the plurality of surgical staples and a staple guide member configured to guide ejection of the surgical staples from the stapling assembly.

In embodiments, the handle portion is formed from first and second handle sections movable relative to one another between a closed configuration and an open configuration. The handle portion may further include a chassis interconnecting the first and second handle sections. The chassis may also be configured to support a portion of the approximation assembly and/or a portion of the firing assembly.

In embodiments, the elongated body portion defines a curved configuration and the pusher link includes a plurality of link segments pivotably coupled to one another to facilitate translation of the pusher link through the curved elongated body portion. The link segments may be pivotably coupled to one another via a ball-and-socket joint(s).

Also provided in accordance with the present disclosure is a method of surgery. The method includes providing a surgical stapling apparatus including a handle portion formed from first and second handle sections, an elongated body portion extending distally from the handle portion and having an engagement member coupled to a distal portion of the elongated body portion, a firing assembly, an approximation assembly, an anvil assembly disposed at a distal end of the approximation assembly, and a first stapling assembly housing a first plurality of surgical staples. The first stapling assembly is engaged to the engagement member of the elongated body portion. The surgical stapling apparatus may otherwise be configured similar to any of the embodiments described herein. The method further includes inserting the surgical stapling apparatus into an internal surgical site, actuating the approximation assembly to clamp tissue between the first stapling assembly and the anvil assembly, actuating the firing assembly to eject the first plurality of surgical staples from the first stapling assembly, through the clamped tissue, and into the anvil assembly to form the first plurality of surgical staples about the clamped tissue, removing the surgical stapling apparatus from the internal surgical site, and disengaging the first stapling assembly from the engagement member.

In embodiments, the method further includes moving the first and second handle sections relative to one another from a closed position to an open position, disengaging the handle portion, the elongated body portion, the anvil assembly, the firing assembly, and the approximation assembly from one another, sterilizing the handle portion, the elongated body portion, the anvil assembly, the firing assembly, and the approximation assembly, reengaging the handle portion, the elongated body portion, the anvil assembly, the firing assembly, and the approximation assembly to one another, moving the first and second handle sections relative to one another from the open position back to the closed position, and engaging a second stapling assembly with the engagement member. The second stapling assembly houses a second plurality of surgical staples.

In embodiments, the method further includes inserting the surgical stapling apparatus into an internal surgical site, actuating the approximation assembly to clamp tissue between the second stapling assembly and the anvil assembly, and actuating the firing assembly to eject the second plurality of surgical staples from the second stapling assembly, through the clamped tissue, and into the anvil assembly to form the second plurality of surgical staples about the clamped tissue. See also, for example, U.S. Pat. No. 7,857,187 to Milliman, previously incorporated by reference herein, U.S. Pat. No. 6,945,444 to Gresham et al., the entire contents of which are incorporated by reference herein, and U.S. Pat. No. 7,303,106 to Milliman et al., the entire contents of which are incorporated by reference herein.

BRIEF DESCRIPTION OF THE DRAWINGS

Various embodiments of the presently disclosed surgical stapling apparatus are described herein with reference to the drawings wherein:

FIG. 1 is a top, side, perspective view from the distal end of one embodiment of the presently disclosed surgical stapling apparatus;

FIG. 2 is an enlarged view of the area of detail indicated as "2" in FIG. 1;

FIG. 3 is a side view of the surgical stapling apparatus shown in FIG. 1 with the anvil assembly removed;

FIG. 4 is a top, side, perspective view from the proximal end of the surgical stapling apparatus shown in FIG. 1 with the anvil assembly removed;

FIG. 14 is an exploded, perspective view of the replaceable stapling assembly of the surgical stapling apparatus shown in FIG. 1;

FIG. 15 is an enlarged view of the area of detail indicated as "15" in FIG. 14;

FIG. 19 is a longitudinal, cross-sectional view taken along section line 19-19 of FIG. 18;

FIG. 20 is a longitudinal, cross-sectional view of the replaceable stapling assembly and the distal end of the firing assembly shown disengaged from one another;

FIG. 21 is a longitudinal, cross-sectional view of the replaceable stapling assembly and the distal end of the firing assembly shown engaged to one another;

FIG. 28 is a top, side, perspective view of the approximation assembly of the surgical stapling apparatus shown in FIG. 1;

FIG. 29 is an enlarged view of the area of detail indicated at "29" in FIG. 28;

FIG. 30 is an exploded, side, perspective view of the approximation assembly of the surgical stapling apparatus shown in FIG. 1;

FIG. 34 is a longitudinal, cross-sectional view of the pusher link assembly shown in FIG. 31;

FIG. 35 is a longitudinal, cross-sectional view of the pusher link assembly shown in FIG. 34 with the inner tube in a further articulated position;

FIG. 45 is a top view of the surgical stapling apparatus of FIG. 1 in the approximated position;

FIG. 46 is an enlarged view of the area of detail indicated as "46" in FIG. 45;

DETAILED DESCRIPTION OF EMBODIMENTS

Figure 5:
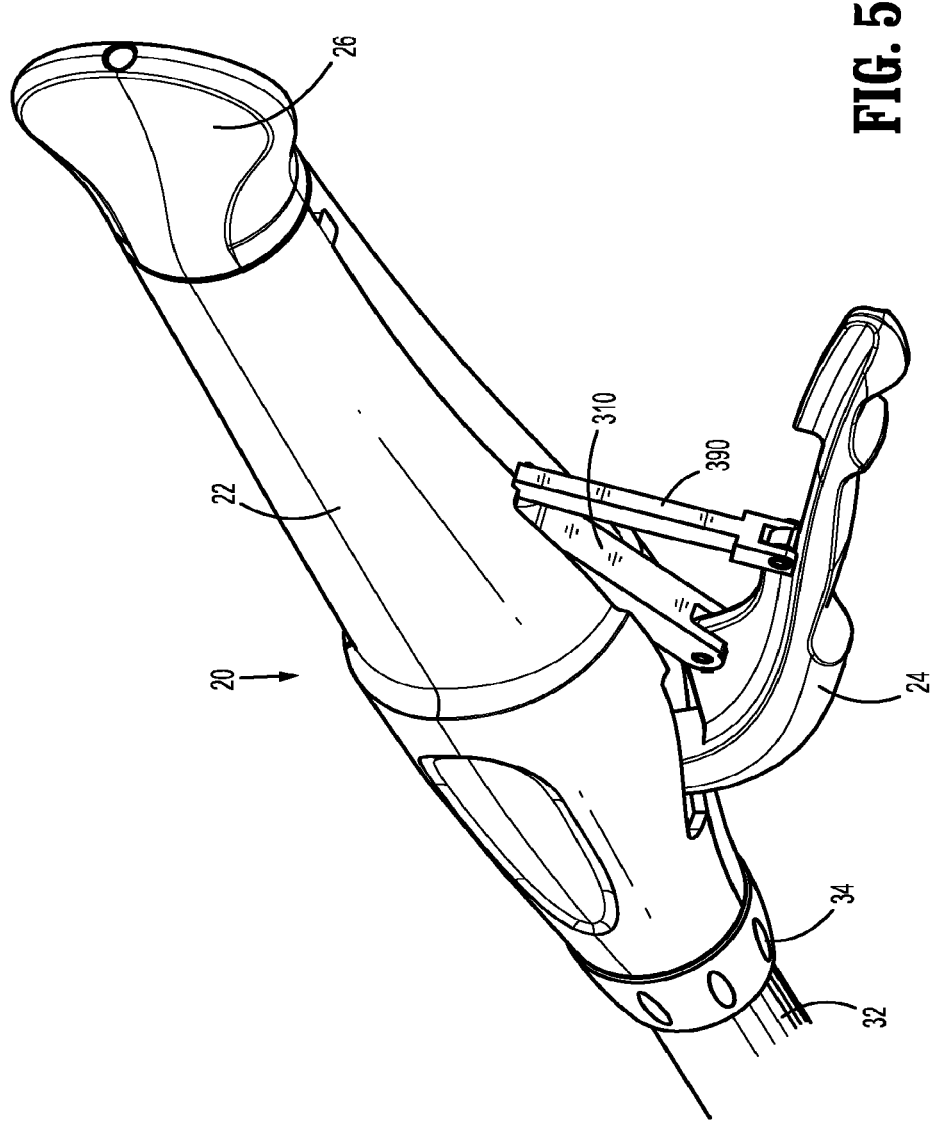
FIG. 5 is a bottom, side, perspective view of the handle portion of the surgical stapling apparatus shown in FIG. 1.
Figure 6:
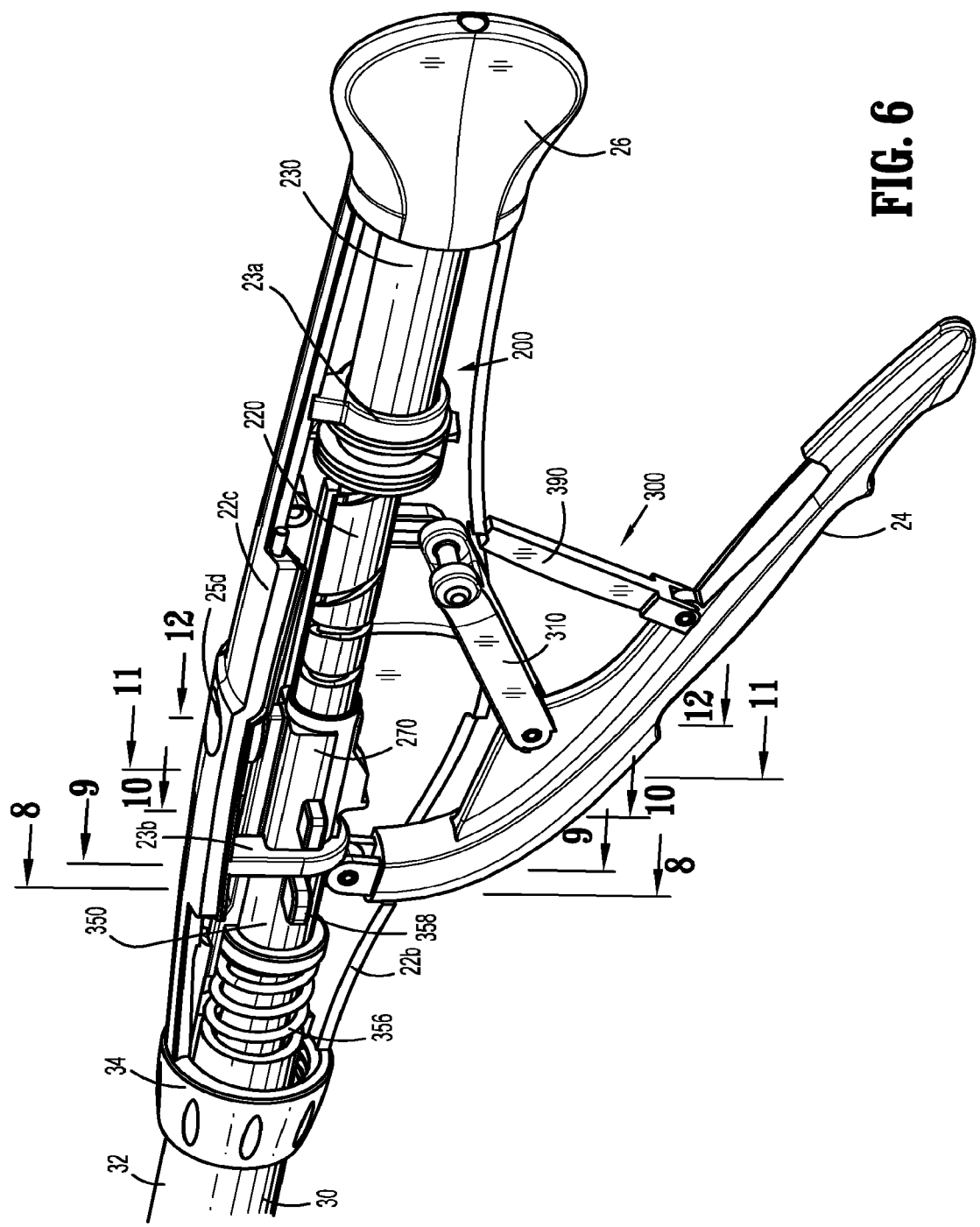
FIG. 6 is a side, perspective view of the handle portion of the surgical stapling apparatus shown in FIG. 1 with one of the handle sections removed to show the internal components of the handle portion.
Figure 7:
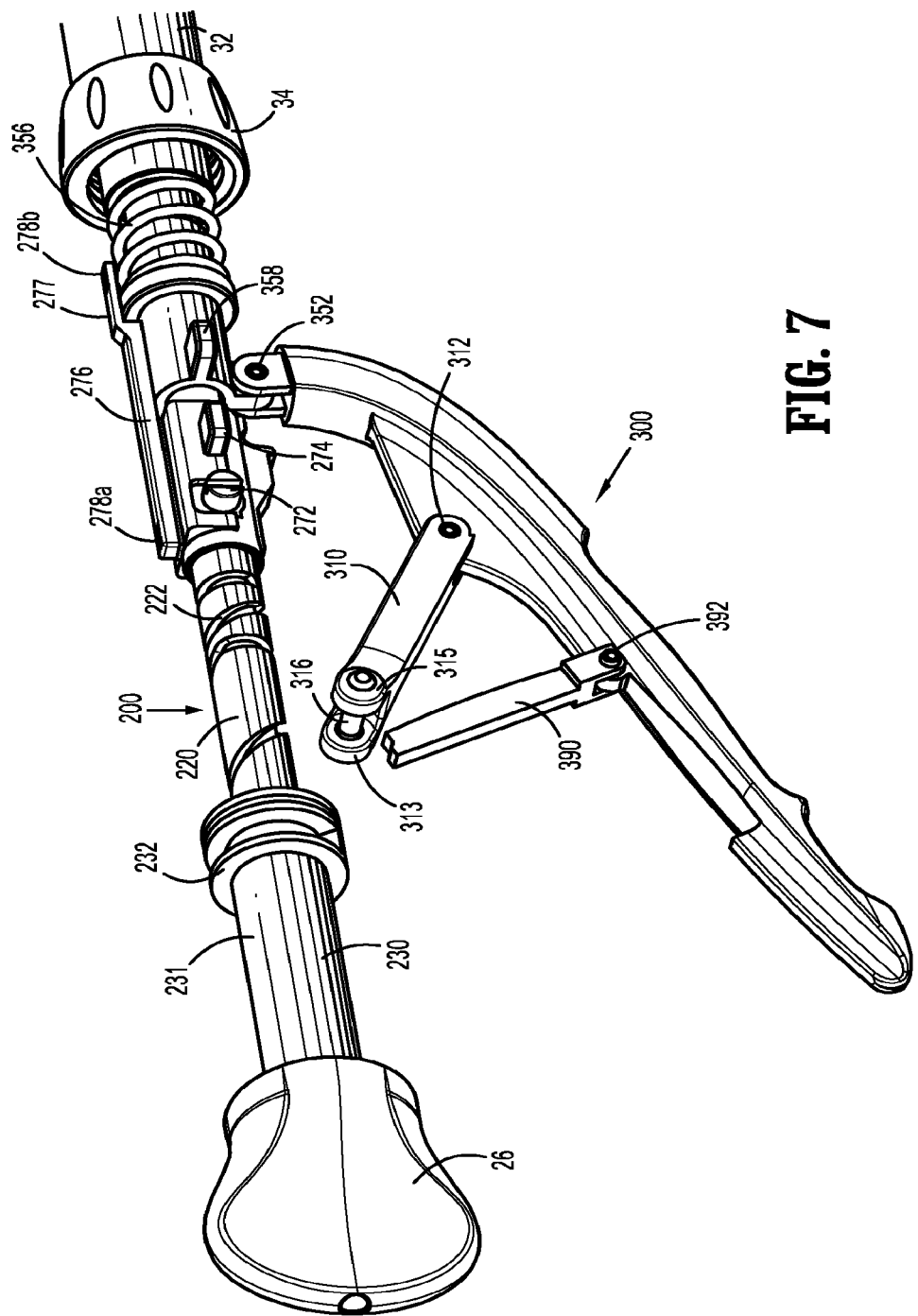
FIG. 7 is a side, perspective view of the proximal end of the handle portion of the surgical stapling apparatus of FIG. 1 with the handle sections removed and the proximal portions of the firing assembly and approximation assembly illustrated.
Figure 8:
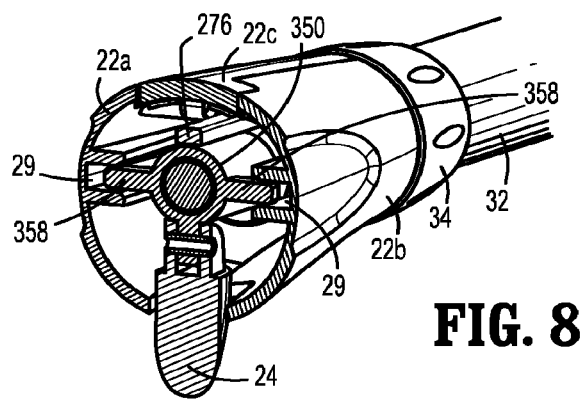
FIG. 8 is a transverse, cross-sectional view taken along section line 8-8 of FIG. 6.
Figure 9:
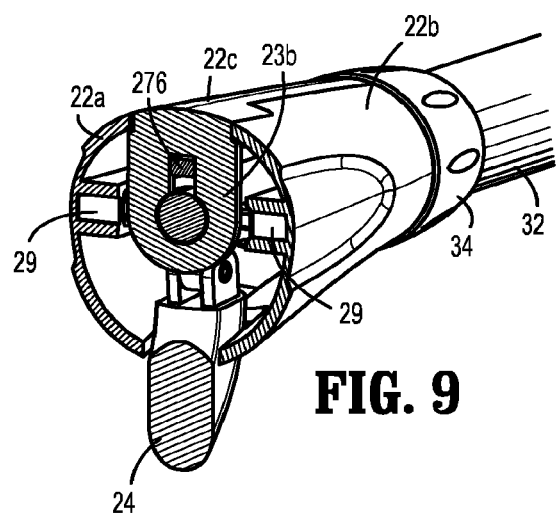
FIG. 9 is a transverse, cross-sectional view taken along section line 9-9 of FIG. 6.
Figure 10:
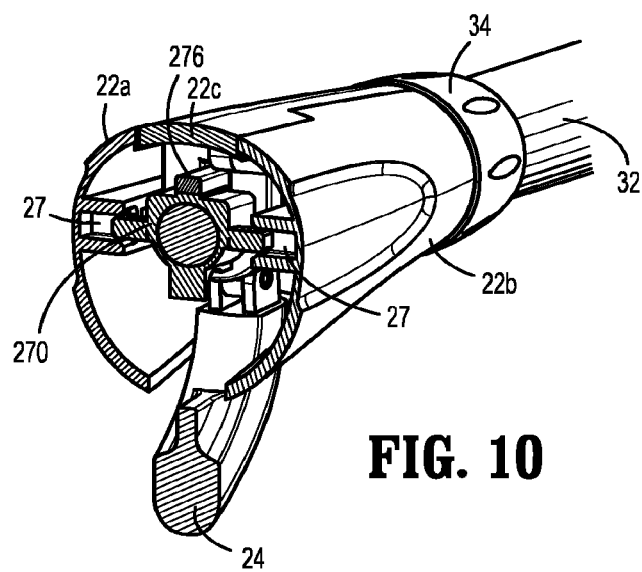
FIG. 10 is a transverse, cross-sectional view taken along section line 10-10 of FIG. 6.
Figure 11:
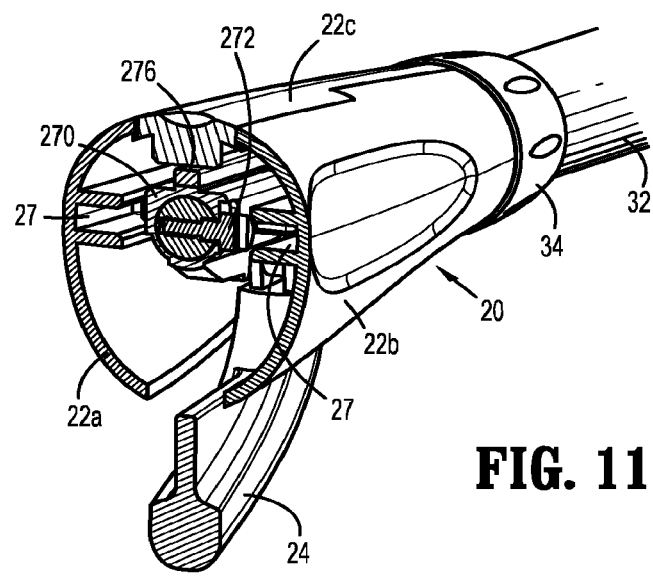
FIG. 11 is a transverse, cross-sectional view taken along section line 11-11 of FIG. 6.
Figure 12:
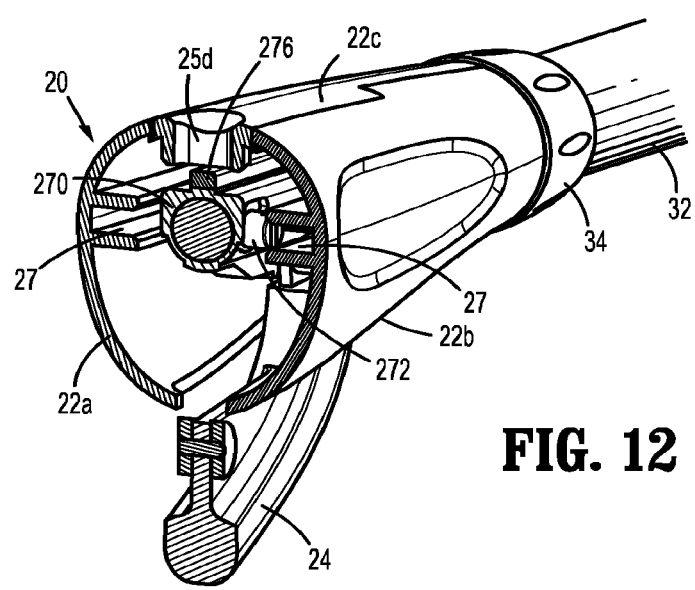
FIG. 12 is a transverse, cross-sectional view taken along section line 12-12 of FIG. 6.
Figure 13:
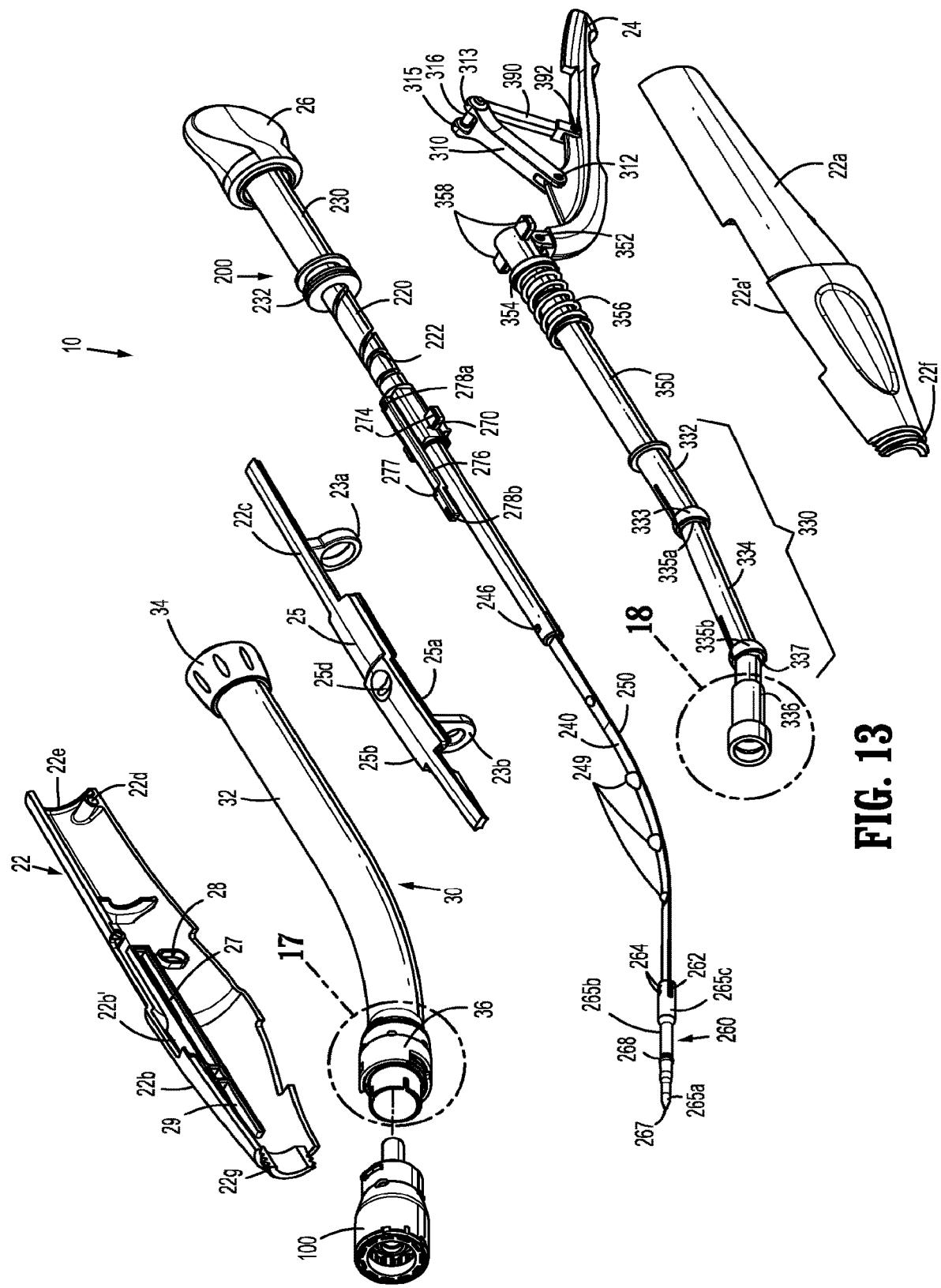
FIG. 13 is an exploded, perspective view of the surgical stapling apparatus shown in FIG. 1.

Embodiments of the presently disclosed surgical stapling apparatus will now be described in detail with reference to the drawings in which like reference numerals designate identical or corresponding elements in each of the several views. Throughout this description, the term "proximal" will refer to the portion of the apparatus closest to the user and the term "distal" will refer to the portion of the apparatus farthest from the user.

With general reference to FIGS. 1-49, an embodiment of the presently disclosed surgical stapling apparatus is shown identified by reference numeral 10. Surgical stapling apparatus 10 includes a proximal handle portion 20, an elongated central body portion 30, and a distal head portion 40. With particular reference to FIGS. 1-3 and 5-7, proximal handle portion 20 includes a stationary handle 22, a firing trigger 24, and a rotatable approximation knob 26. Stationary handle 22 is formed from first and second releasably engagable handle sections 22a, 22b and a support chassis 22c (see FIGS. 36-37) that cooperate to house and support the internal components of handle portion 20, e.g., the proximal components of approximation assembly 200 and firing assembly 300. Proximal handle portion 20 and the internal components thereof will be described in greater detail below.

With particular reference to FIGS. 1 and 13-16, elongated central body portion 30 of surgical stapling apparatus 10 includes a curved elongated outer tube 32, a proximal bushing 34, and a distal engagement shell 36. Outer tube 32 is configured to receive components of approximation assembly 200 and firing assembly 300. As will be discussed in further detail below, proximal bushing 34 is provided to facilitate releasable threaded engagement of the proximal end of outer tube 32 with stationary handle 22 of handle portion 20. In addition, engagement shell 36 is provided to facilitate releasable engagement of replaceable stapling assembly 100 with the distal end of outer tube 32.

Distal head portion 40 of surgical stapling apparatus 10 includes an anvil assembly 400 (FIG. 1) that is releasably engagable with the distal end of approximation assembly 200 (FIG. 28), and a replaceable stapling assembly 100 that is releasably engagable with the distal end of elongated central body portion 30. Replaceable stapling assembly 100 (or portions thereof) is configured as a disposable component that is to be replaced with a new replaceable stapling assembly 100 (or portions thereof) after each firing. The remaining components of surgical stapling apparatus 10 are configured as reusable, sterilizable components, although one or more of these components may alternatively be configured as a disposable component. Distal head portion 40 will be described in greater detail below.

The various components of surgical stapling apparatus 10 described hereinbelow are configured to facilitate the assembly and disassembly of surgical stapling apparatus 10, thus facilitating the disposal and replacement of those components that are disposable and the sterilization and reassembly of those components that are reusable. The materials used to form the various components of surgical stapling apparatus 10 will depend upon the strength requirements of the particular component and the use requirements of the particular component, e.g., whether the component is reusable or disposable. The reusable components, for example, may generally be formed from thermoplastics including polycarbonates, and metals including stainless steel and aluminum, that are suited to withstand repeated sterilization procedures, e.g., autoclaving.

Referring to FIGS. 1, 6, 7, 13, and 28-30, approximation mechanism 200 of surgical stapling apparatus 10 includes an approximation knob 26, a drive screw 220, a rotatable sleeve 230, first and second screw extensions 240 and 250, respectively, and an anvil retainer 260. Rotatable sleeve 230 includes a substantially cylindrical hollow body portion 231 and a substantially cylindrical collar 232 that together define a central bore 233 (FIG. 30). Body portion 231 is supported within proximal handle portion 20 via proximal support ring 23a (FIG. 13) of support chassis 22c, as will be described in greater detail below. The proximal end of body portion 231 of rotatable sleeve 230 extends through an opening 22e in the proximal end of stationary handle 22. A pair of diametrically opposed ribs 235 are positioned or formed on the outer surface of body portion 231. Approximation knob 26 includes a pair of internal slots (not shown) positioned to receive ribs 235 of sleeve 230 to rotatably fix sleeve 230 to knob 26 such that rotation of knob 26 effects similar rotation of sleeve 230. Greater or fewer ribs 235 and slots 212 may alternatively provided. Further, this configuration may be reversed, e.g., where ribs 235 are disposed on approximation knob 26 and slots 212 are defined within sleeve 230. Collar 232 is positioned distally of and in abutment with proximal support ring 23a of support chassis 22c, while approximation knob 26 is positioned proximally of and in abutment with the proximal end of stationary handle 22 such that sleeve 230 is axially fixed relative to stationary handle 22 but permitted to rotate relative to stationary handle 22.

Referring to FIGS. 29 and 30, the proximal portion of screw 220 includes a helical channel 222 and is dimensioned to be slidably positioned within central bore 233 of rotatable sleeve 230. A tracking pin 224 extends through cylindrical collar 232 of sleeve 230 into helical channel 222 of screw 220. Tracking pin 224 is secured to cylindrical collar 232 such that rotation of cylindrical collar 232 effects similar rotation of tracking pin 224. The pitch of helical channel 222 may vary along the length of drive screw 220, as will be described below, or may be constant along the length of drive screw 220.

With additional reference to FIGS. 1, 6, 7, and 13, screw 220 is supported within proximal handle portion 20 towards the distal end thereof via distal support ring 23b of support chassis 22c, as will be described in greater detail below. The distal end of screw 220 includes a transverse slot 226. First and second screw extensions 240 and 250 each include a flexible band portion 242 and 252, although other configurations are also contemplated. In some embodiments, first screw extension 240 or second screw extension 250 may contain a flexible band portion while the other one does not. The flexibility of the flexible band portion may be accomplished in any number of ways. For example, the flexible band portion may be constructed of a flexible material. In an embodiment, the flexible band portion may include a plurality of segments. In an embodiment, the flexible band portion may have material removed from it, for example in notches, to increase flexibility. The flexibility of band portions 242 and 252 permits translation of screw extensions 240 and 250 through curved elongated outer tube 32 of elongated body portion 30. The proximal end of each band portion 242 and 252 includes a respective hole 244 and 254 dimensioned to receive a pin 246 for securing the proximal end of screw extensions 240 and 250 within transverse slot 226 of screw 220. The band portions 242 and 252 of each screw extension 240 and 250 are dimensioned to be received within a transverse slot 262 formed in a proximal end of anvil retainer 260 to fasten anvil retainer 260 to the distal end of screw extensions 240 and 250. More specifically, a pair of pins 264 extends through the proximal end of anvil retainer 260 and band portions 240 and 250 to secure screw extensions 240 and 250 to anvil retainer 260. Alternately, other fastening techniques may be used to secure screw extensions 240, 250 to anvil retainer 260 and screw 220, e.g., friction fitting, welding, crimping, etc.

As shown in FIG. 30, one or both of the screw extensions 240, 250, e.g., screw extension 240, includes a plurality of apertures 248 defined along the length of the screw extension 240. Apertures 248 are configured to support a spacer member 249. Each spacer member 249 includes a protrusion 249a (FIG. 39) which is received within a respective aperture 248 to secure the spacer members 249 to the screw extension 240. Each spacer member 249 further includes a head positioned to extend outwardly from screw extension 240. The heads of spacer members 249 maintain alignment and guide translation of screw extensions 240, 250 through curved elongated outer tube 32 of elongated central body portion 30. Further, the spacer members 249 may define various different size configurations, e.g., where spacer members 249 disposed towards the middle of screw extension 240 have larger heads as compared to those disposed towards either end of screw extension 240. As can be appreciated, the larger heads are positioned at the points of relatively greater bending, e.g., towards the middle of screw extension 240, although other configurations are also contemplated.

With reference to FIGS. 28 and 30, anvil retainer 260 includes a trocar portion 265a, a body portion 265b, and an attachment portion 265c. Trocar portion 265a includes a blunt trocar tip 267, although other configurations are also contemplated. Body portion 265b is substantially cylindrical and has a diameter which is larger than the diameter of trocar portion 265a. An annular protrusion 268 is disposed about body portion 265b of anvil retainer 260 and is configured to engage anvil assembly 400 (FIG. 1) to retain anvil assembly 400 (FIG. 1) about anvil retainer 260, as will be described in greater detail below.

Referring to FIGS. 1, 6, 7, 13, and 28-30, in use, when approximation knob 26 is manually rotated, rotatable sleeve 230 is likewise rotated about the proximal end of screw 220. Since sleeve 230 is axially fixed with respect to stationary handle 22, and with tracking pin 224 disposed within helical channel 222 and rotationally fixed relative to sleeve 230, axial rotation of sleeve 230 about screw 220 causes tracking pin 224 to move along channel 222 of screw 220 to thereby urge screw 220 to translate axially within stationary handle 22 relative to sleeve 230. Upon axial translation of screw 220, first and second screw extensions 240 and 250, which are fastened to the distal end of screw 220, and anvil retainer 260, which is fastened to the distal end of screw extensions 240 and 250, are moved axially through outer tube 32 of elongated body portion 30. Thus, with anvil assembly 400 (FIG. 1) releasably engaged about the distal end of anvil retainer 260, knob 26 may be rotated to effect movement of anvil assembly 400 (FIG. 1) relative to stapling assembly 100 between spaced-apart and approximated positions, i.e., to move anvil assembly 400 (FIG. 1) closer to or further from stapling assembly 100, depending on the direction of rotation of knob 26. In embodiments, as mentioned above, the pitch of helical channel 222 may vary along the length of drive screw 220 so as to provide finer control of the positioning of anvil assembly 400 (FIG. 1) as anvil assembly 400 (FIG. 1) approaches the approximated position. That is, the distal portion of helical channel 222 may define a reduced pitch as compared to the proximal portion of helical channel 222 such that rotation of knob 26 translates anvil assembly 400 (FIG. 1) a relatively shorter distance per revolution of knob 26 as anvil assembly 400 (FIG. 1) approaches the approximated position to provide for finer or more accurate adjustment of the positioning of anvil assembly 400 (FIG. 1) as the anvil assembly 400 nears the approximated position.

With reference to FIGS. 28-30 and 42, approximation assembly 200 further includes a screw stop 270 disposed about screw 220 and configured to function as a proximal stop for defining the minimum tissue receiving clearance between anvil assembly 400 and stapling assembly 100. Screw stop 270 includes a cam adjustment member 272 that allows the minimum tissue gap defined between the stapling assembly 100 and the anvil assembly 400 to be selectively adjusted. Screw stop 270 includes a pair of wings 274 that extend radially outwardly from screw stop 270. Wings 274 are dimensioned to slide along channels 27 (FIGS. 10-12) formed along the interior walls of handle sections 22a, 22b of stationary handle 22 to maintain proper alignment and guide translation of approximation assembly 200 through stationary handle 22. Upon reaching the proximal ends of channels 27 (FIGS. 10-12) of handle sections 22a, 22b, wings 274 inhibit further proximal translation of screw 220 and, thus, further approximation of anvil assembly 400 to define the minimum tissue gap between anvil assembly 400 and stapling assembly 100. Cam adjustment member 272 is described in greater detail in U.S. Pat. No. 7,857,187 to Milliman, previously incorporated by reference herein in its entirety.

Figure 44:
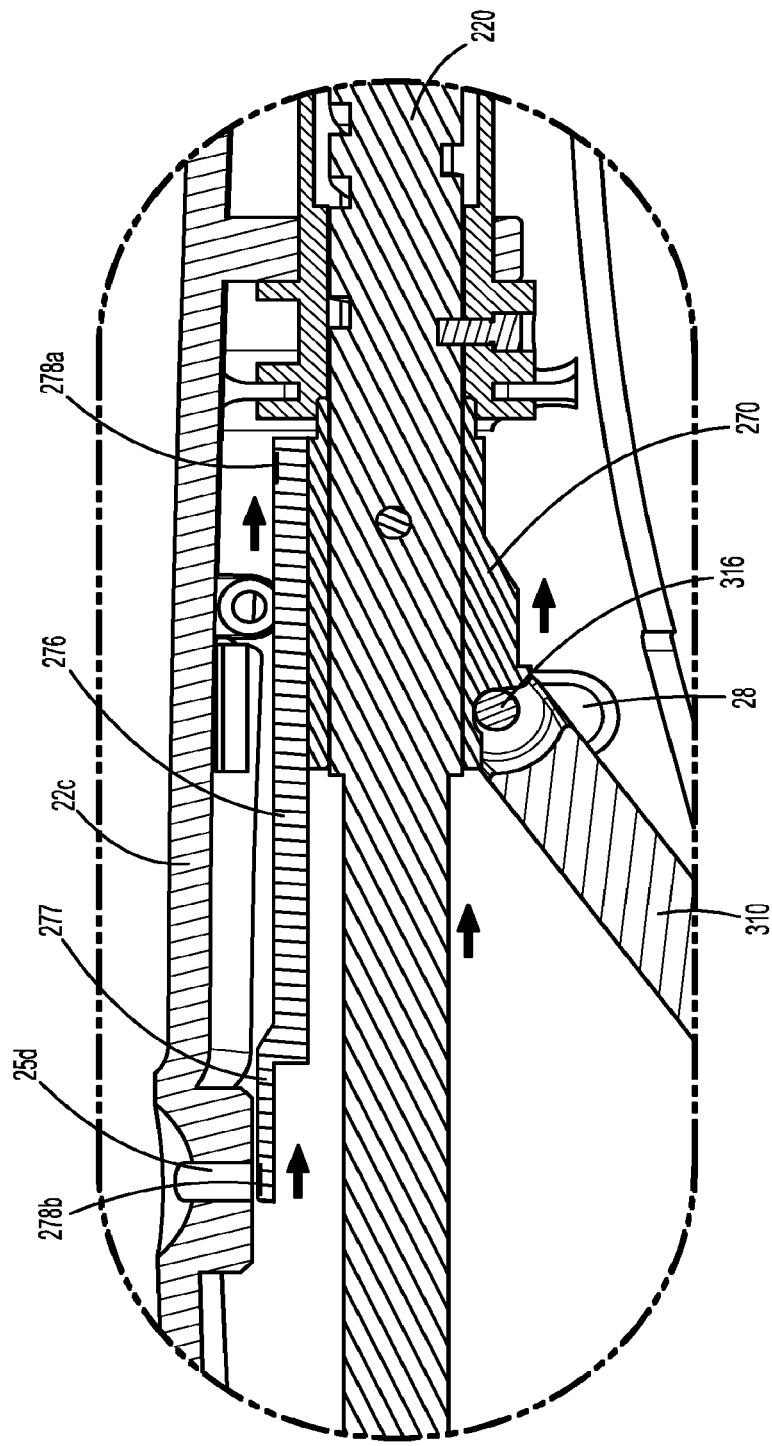
FIG. 44 is an enlarged, cross-sectional view of the area of detail indicated as "44" in FIG. 43.

With additional reference to FIGS. 1, 2, 45, and 46, a visual indicator bar 276 is fixedly supported on the screw stop 270 and extends distally therefrom. Indicator bar 276 may be secured to screw stop 270 via adhesives, snap-fitting, screws, or any other suitable securement mechanism or process. Visual indicator bar 276 includes a stepped distal portion 277 and first and second visual indicators 278a, 278b disposed at respective proximal and distal ends thereof. Visual indicators 278a, 278b may be of any suitable color(s), symbol(s) or may include any other suitable feature, e.g., reflective features, a light source (LED), etc., to facilitate the visualization of visual indicator 278a through window 25d of proximal handle portion 20 (see FIG. 2). Visual indicator 278a provides an indication that the anvil assembly 400 (FIG. 1) is disposed in the spaced-apart or unapproximated position (FIG. 41) when visual indicator 278a is visible through window 25d of proximal handle portion 20. Similarly, when visual indicator 278b is visible through window 25d of proximal handle portion 20 an indication is provided that the anvil assembly 400 (FIG. 1) is disposed in the approximated position (FIG. 44). It is envisioned that visual indicators 278a, 278b are different from one another to allow a user to quickly ascertain whether anvil assembly 400 (FIG. 1) is disposed in the spaced-apart position, the approximated position, or a positioned therebetween, e.g., wherein neither visual indicator 278a nor visual indicator 278b is visible through window 25d of proximal handle portion 20. Other suitable indicator mechanisms are disclosed in U.S. Pat. No. 7,857,187 to Milliman and U.S. Pat. No. 6,945,444 to Gresham et al., previously incorporated by reference herein in their entirety.

Referring to FIGS. 3-7, firing assembly 300 includes firing trigger 24, a firing link 310, a safety bar 390, an elongated tubular pusher link assembly 330, and a coupling member 350. The distal end of firing trigger 24 is pivotally connected to coupling member 350 by a pivot member 352. Coupling member 350, in turn, is secured to the proximal segment 332 of elongated tubular pusher link assembly 330 using any known fastening technique. Alternatively, coupling member 350 may be formed integrally with the proximal segment 332 of pusher link assembly 330. Coupling member 350 includes a flange 354 that is configured to maintain a spring 356 between a proximal end of outer tube 32 of elongated body portion 30 and flange 354. Spring 356 biases pusher link assembly 330 proximally towards a retracted, non-fired position. A pair of wings 358 extend radially outwardly from coupling member 350. Wings 358 are dimensioned to slide along channels 29 formed along the interior walls of handle sections 22a, 22b of stationary handle 22 to maintain proper alignment and guide translation of coupling member 350 and pusher link 330 through stationary handle 22 (see FIGS. 8 and 9). Other suitable mechanisms for maintaining alignment and guiding translation of coupling member 350 are also contemplated, e.g., tabs and protrusions, ribs and recesses, etc.

With additional reference to FIGS. 31-35, elongated tubular pusher link assembly 330 is formed from a plurality of segments, e.g., proximal, intermediate, and distal segments 332, 334, 336, respectively, that are articulatable relative to one another to facilitate translation of elongated tubular pusher link assembly 330 through curved elongated outer tube 32 of elongated body portion 30. Each segment 332, 334, 336 defines a hollow interior configured to slidably receive the distal portion of approximation assembly 200. Proximal segment 332, as mentioned above, is fastened to or formed integrally with coupling member 350 at the proximal end of proximal segment 332. A spherical socket 333 is formed at the distal end of proximal segment 332. Intermediate segment 334 defines a spherical ball 335a at the proximal end thereof that is configured for receipt within spherical socket 333 of proximal segment 332 for engaging proximal and intermediate segments 332, 334, respectively, to one another while permitting rotation and articulation of proximal and intermediate segments 332, 334, respectively, relative to one another. Similarly, a spherical socket 335b is formed at the distal end of intermediate segment 334 and a spherical ball 337 configured for receipt within spherical socket 335b is defined at the proximal end of distal segment 336 for engaging intermediate and distal segments 334, 336, respectively, to one another while permitting rotation and articulation of intermediate and distal segments 334, 336, respectively, relative to one another. The distal end of distal segment 336 includes a collar portion 338 defining an annular recess 339 on an interior surface thereof for releasably engaging cartridge assembly 110 (see FIGS. 20-21) therein, as will be described in greater detail below.

Firing link 310 has a distal end pivotally secured to firing trigger 24 by a pivot member 312 and a proximal end that is pivotably secured to stationary handle 22. More specifically, the proximal end of firing link 310 defines a bifurcated configuration having first and second flanges 313, 315 that are configured to receive a pivot member 316 therethrough. Pivot member 316 extends between and outwardly from each of first and second flanges 313, 315 for receipt within vertical slots 28 (FIG. 37) formed within each of handle sections 22a and 22b, respectively. As such, pivot member 316 is free to move vertically within slots 28 (FIG. 37) but is substantially inhibited from horizontal translation relative to stationary handle 22, thus inhibiting the proximal end of firing link 310 from horizontal translation relative to stationary handle 22.

Safety bar 390 is pivotably coupled to firing trigger 24 at a first end of safety bar 390 via a pivot member 392. Safety bar 390 is rotatable between a safe position (FIGS. 40 and 41), wherein the second end of safety bar 390 abuts stationary handle 22 to inhibit actuation of firing trigger 24, and a ready position (FIG. 43), wherein safety bar 390 is positioned within a recess 24a defined in firing trigger 24 to permit actuation of firing trigger 24. Other suitable trigger locks are described in U.S. Pat. No. 7,303,106 to Milliman et al., which is hereby incorporated by reference herein in its entirety, and U.S. Pat. No. 7,857,187 to Milliman and U.S. Pat. No. 6,945,444 to Gresham et al., previously incorporated by reference herein.

Figure 43:
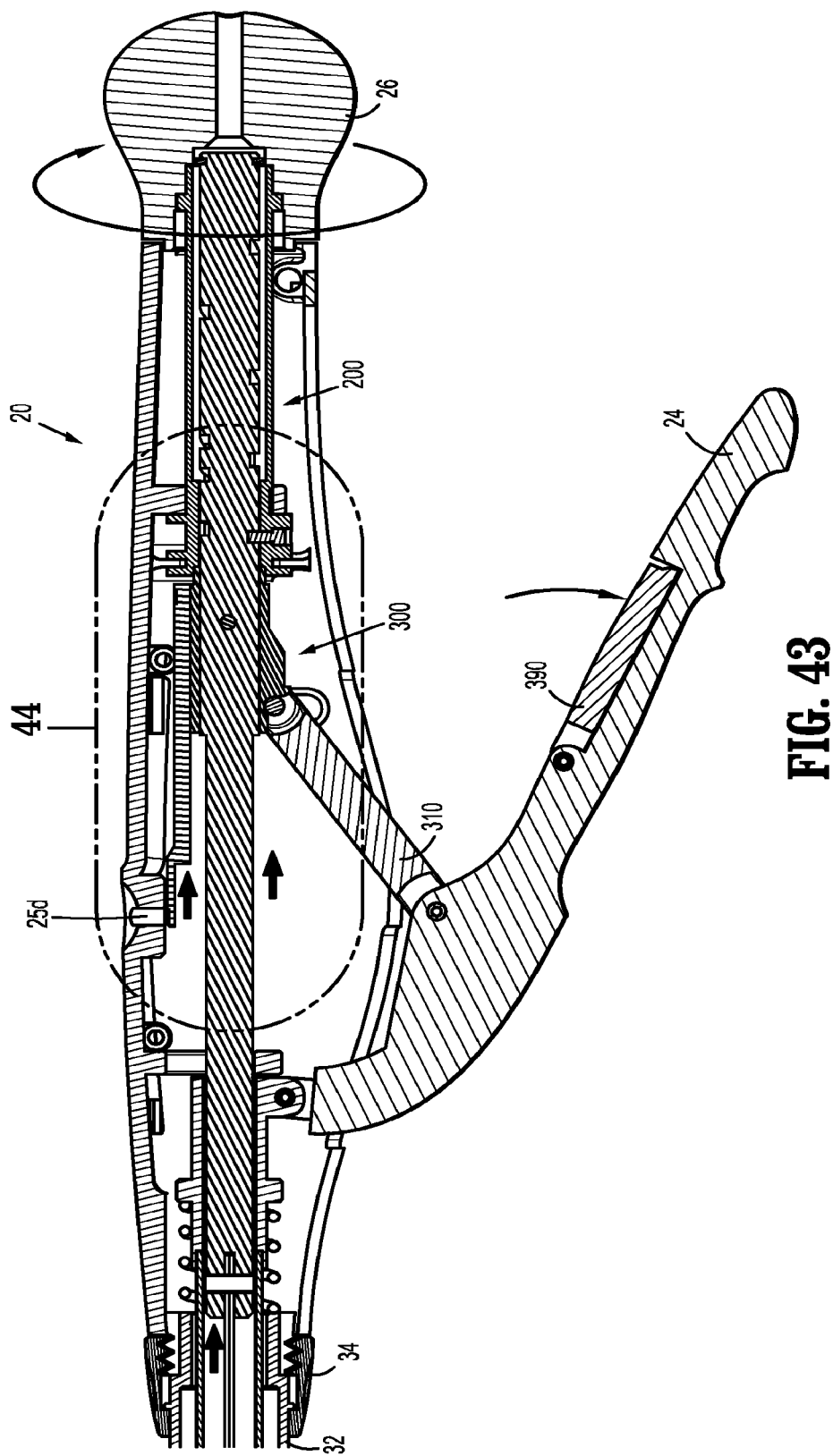
FIG. 43 is a longitudinal, cross-sectional view of the handle portion of the surgical stapling apparatus of FIG. 1 shown in a position corresponding to the approximated position of the surgical stapling apparatus.

With safety bar 390 disposed in the ready position (FIG. 43), firing trigger 24 may be actuated by pivoting firing trigger 24 about pivot members 312, 352 towards stationary handle 22 in a counter-clockwise direction (from the position shown in FIG. 43). Upon actuation of firing trigger 24, firing link 310 is pivoted about pivot member 312 in a clockwise direction (from the position shown in FIG. 43) towards stationary handle 22 to urge firing trigger 24 and coupling member 350 distally relative to stationary handle 22. Distal translation of coupling member 350, in turn, urges pusher link assembly 330 distally against the bias of spring 356. With distal segment 336 of pusher link assembly 330 coupled to pusher 112 of stapling assembly 100, as will be described in greater detail below, distal translation of pusher link assembly 330 may be effected to translate pusher 112 distally through cartridge assembly 110. Thus, as will be described below, actuation of firing trigger 24 may be effected to eject surgical staples 600 from stapling assembly 100. Firing assembly 300 may further include a feedback mechanism similar to that disclosed in U.S. Pat. No. 7,857,187 to Milliman, previously incorporated by reference herein in its entirety.

Figure 47:
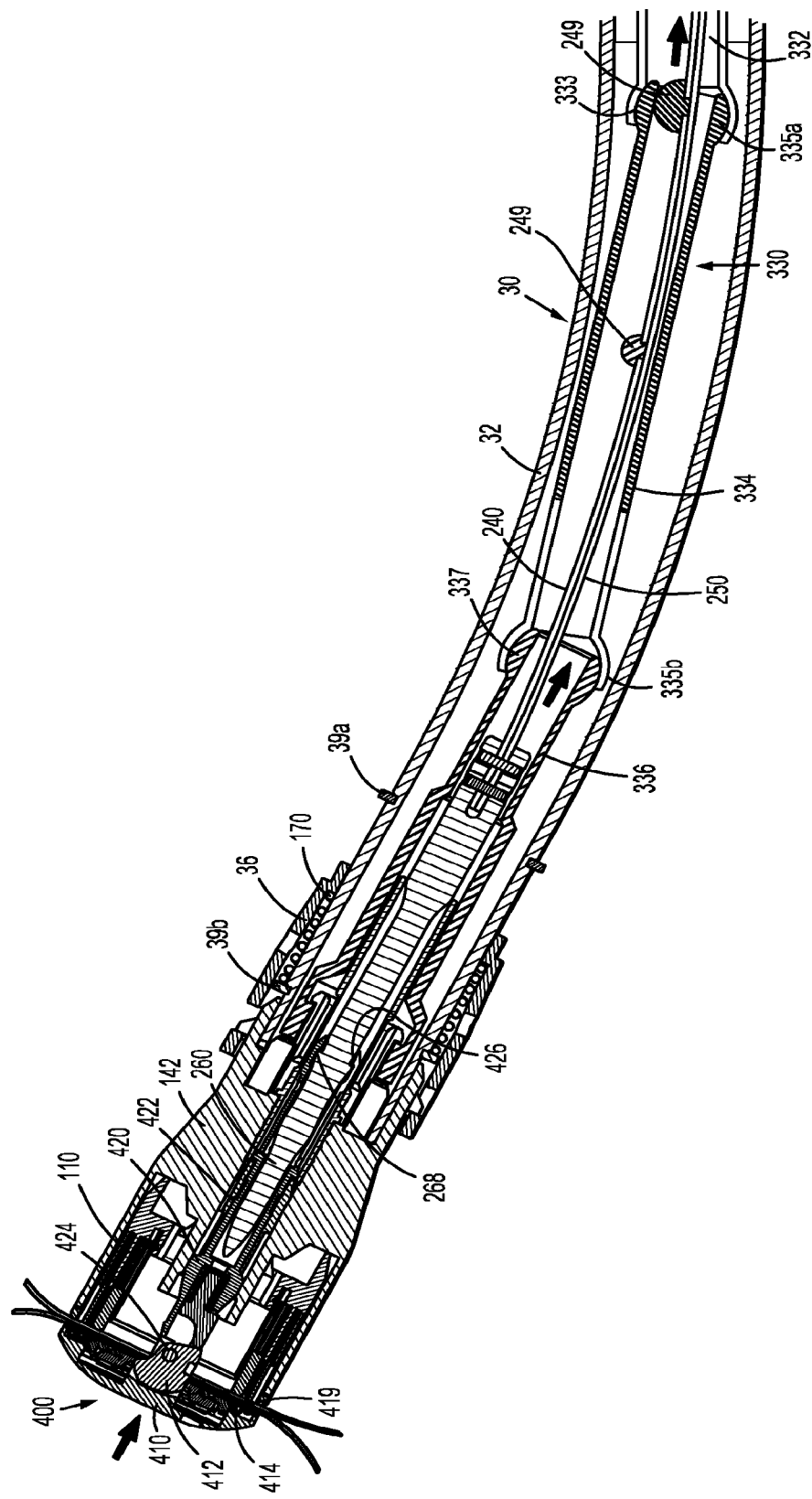
FIG. 47 is a longitudinal, cross-sectional view of the distal end of the surgical stapling apparatus of FIG. 1 shown in the approximated position clamping tissue.
Figure 49:
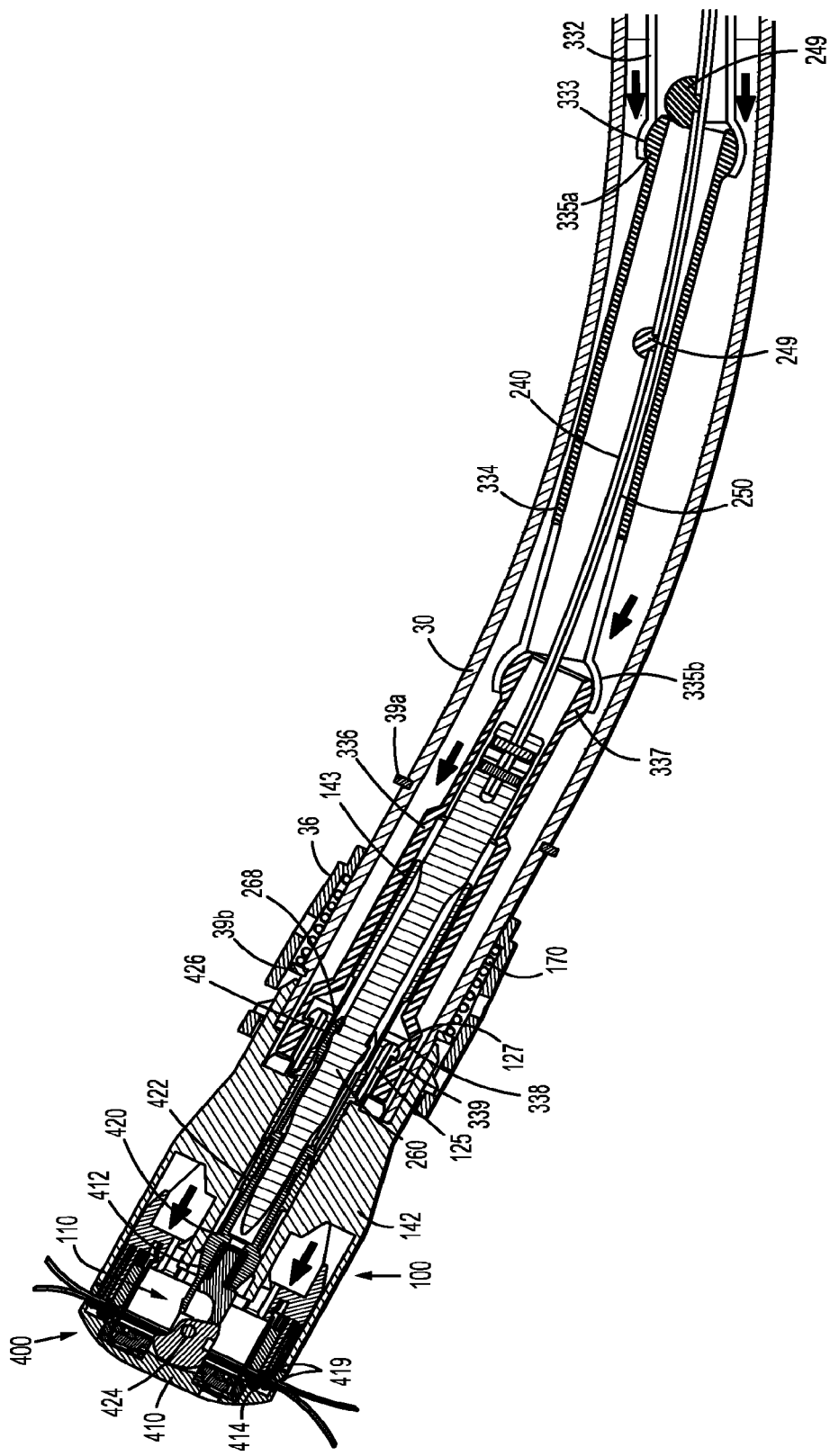
FIG. 49 is a longitudinal, cross-sectional view of the distal end of the surgical stapling apparatus of FIG. 1 shown after firing and formation of the staples about the clamped tissue.

Turning now to FIGS. 1, 47, and 49, anvil assembly 400 includes an anvil head assembly 410 and an anvil center rod assembly 420. Anvil head assembly 410 includes a post 412 and an anvil head 414 that defines a plurality of pockets 419 for receiving and forming staples 600 about tissue. Anvil center rod assembly 420 includes an anvil center rod 422 that is pivotably engaged to post 412 of anvil head assembly 410 via a pivot member 424 to permit anvil head assembly 410 to pivot relative to anvil center rod assembly 420. Anvil center rod 422 defines a hollow interior that is configured to receive anvil retainer 260. Upon insertion of anvil retainer 260 into anvil center rod 422, annular recess 426, which extends inwardly into the hollow interior of anvil center rod 422, receives annular protrusion 268 of anvil retainer 260 such that anvil center rod 422 and, thus, anvil assembly 400 is secured about anvil retainer 260. Anvil assembly 400 may further be configured to include any or all of the features of the anvil assembly described in U.S. Pat. No. 7,857,187 to Milliman or U.S. Pat. No. 6,945,444 to Gresham et al., previously incorporated by reference herein in its entirety.

Turning to FIGS. 1 and 13-27, stapling assembly 100 includes a cartridge assembly 110 and an engagement assembly 140. Cartridge assembly 110 is configured to house a plurality of surgical staples 600 therein and, upon actuation of firing assembly 300, to facilitate the ejection of surgical staples 600 therefrom, through tissue, and into anvil head 414 (FIGS. 47 and 49) for formation of the surgical staples 600 about tissue. Engagement assembly 140 is configured to facilitate operable engagement of stapling assembly 100 to engagement shell 36 at the distal end of outer tube 32 of elongated central body portion 30. Stapling assembly 100 (or component(s) thereof) may be formed as a disposable assembly that is configured to be replaced with a new stapling assembly after each firing.

With particular reference to FIGS. 14, 17, and 19-24, engagement assembly 140 includes a distal shell 142 and an inner extension 143, each of which may be formed from any suitable material, e.g., polyethylene, and is configured as a disposable component. Distal shell 142 includes an outer housing portion 144 and an inner guide portion 146. Inner extension 143 (FIG. 14) is releasably threadingly engagable with inner guide portion 146 of distal shell 142 and is configured to extend proximally therefrom and into distal segment 336 of pusher link assembly 330 to facilitate alignment of cartridge assembly 110 and distal segment 336 of pusher link assembly 330 with one another. Outer housing portion 144 has a distal cylindrical section 147, a central conical section 148, and a proximal cylindrical section 149 that defines a smaller diameter than distal cylindrical section 147. A plurality of openings 150 are formed in conical section 148 to permit fluid and tissue passage during operation of surgical stapling apparatus 10. A pair of diametrically opposed engagement tabs 151, each including an engagement nub 152, is formed on the exterior surface of proximal cylindrical section 149. Engagement tabs 151, as will be described below, are positioned to be received in engagement slots 165 defined within engagement shell 36 of central elongated body portion 30 to facilitate releasable securement of stapling assembly 100 at the distal end of outer tube 32 of elongated body portion 30. Alternatively, this configuration may be reversed, e.g., wherein tabs are provided on engagement shell 36 and slots are defined within cylindrical section 149. Other suitable releasable engagement structure, e.g., bayonet coupling, interference fit, latching, snap-fitting, etc., may also be provided. Distal shell 142 further includes a plurality of spaced-apart orientation bars 154 (FIG. 23) disposed about the interior surface of proximal cylindrical section 149. Orientation bars 154 (FIG. 23) are configured for receipt within slots 33 (FIG. 22) defined about the distal end of outer tube 32 to rotationally fix distal shell 142 about the distal end of outer tube 32 of elongated body portion 30 during assembly. In addition to or as an alternative to orientation bars 154 (FIG. 23), other suitable mechanisms for maintaining alignment are also contemplated, e.g., tabs and protrusions, ribs and recesses, etc.

Figure 16:
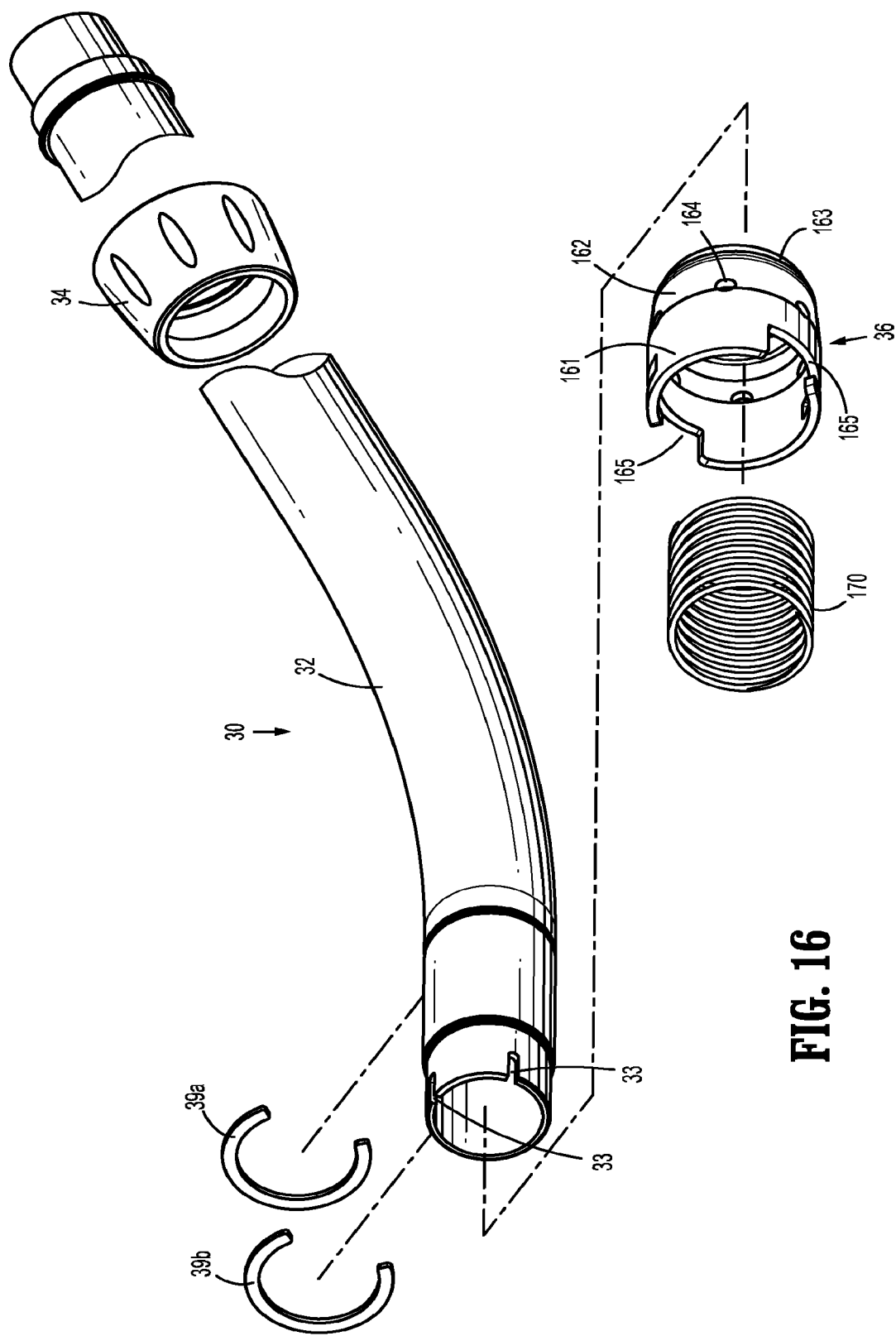
FIG. 16 is an exploded, perspective view of the tube assembly of the surgical stapling apparatus shown in FIG. 1.
Figure 17:
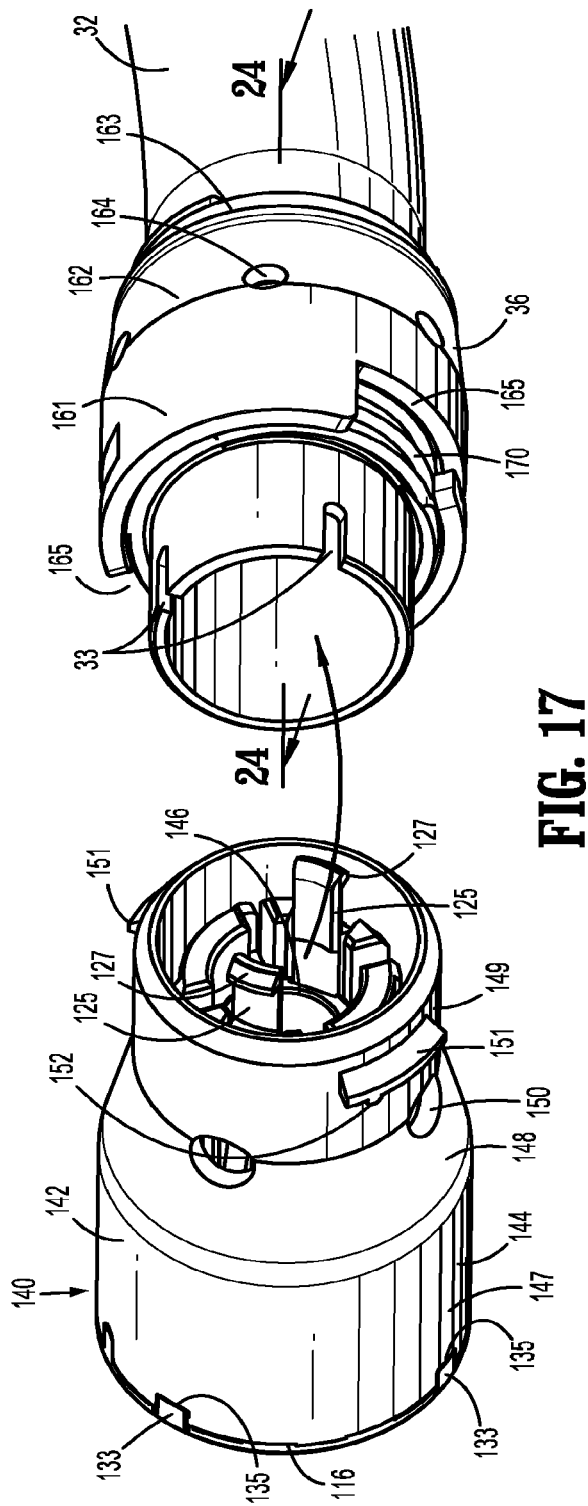
FIG. 17 is an enlarged view of the area of detail indicated as "17" in FIG. 13 spaced from the replaceable stapling assembly of the surgical stapling apparatus shown in FIG. 13.
Figure 18:
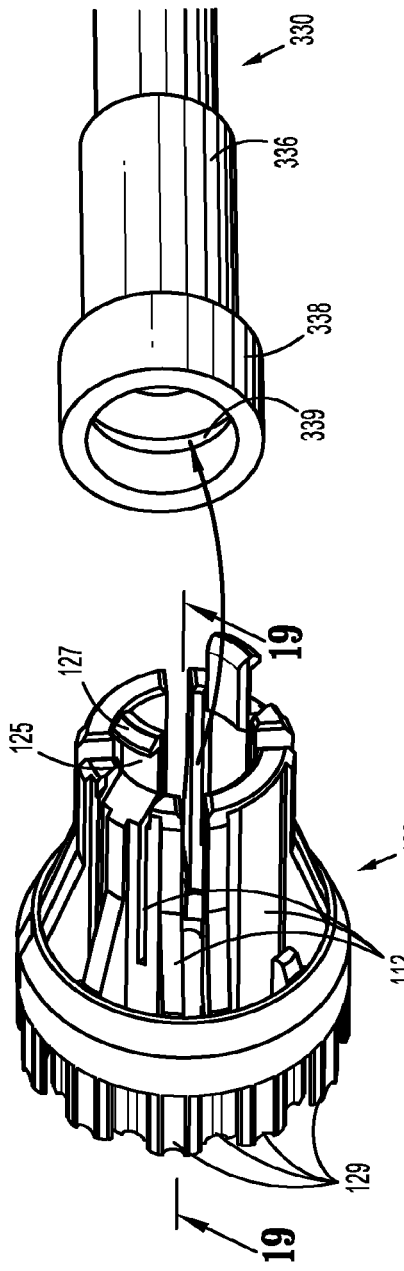
FIG. 18 is an enlarged view of the area of detail indicated as "18" in FIG. 13 spaced from the pusher of the surgical stapling apparatus shown in FIG. 13.
Figure 24:
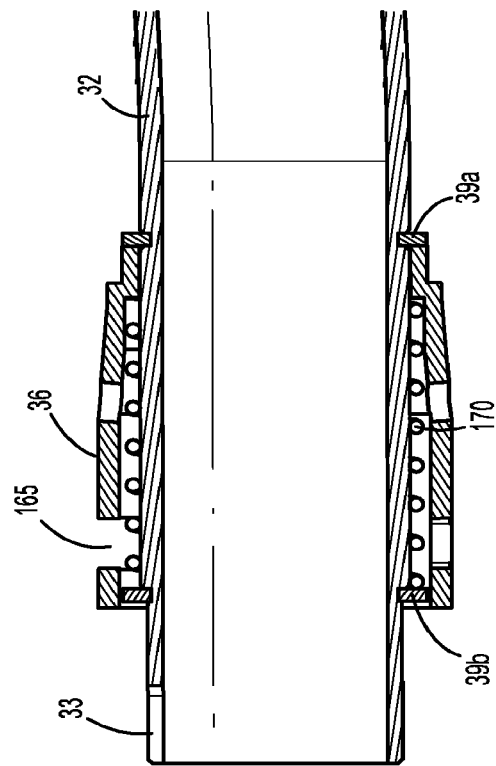
FIG. 24 is a longitudinal, cross-section view taken along section line 24-24 of FIG. 17.
Figure 22:
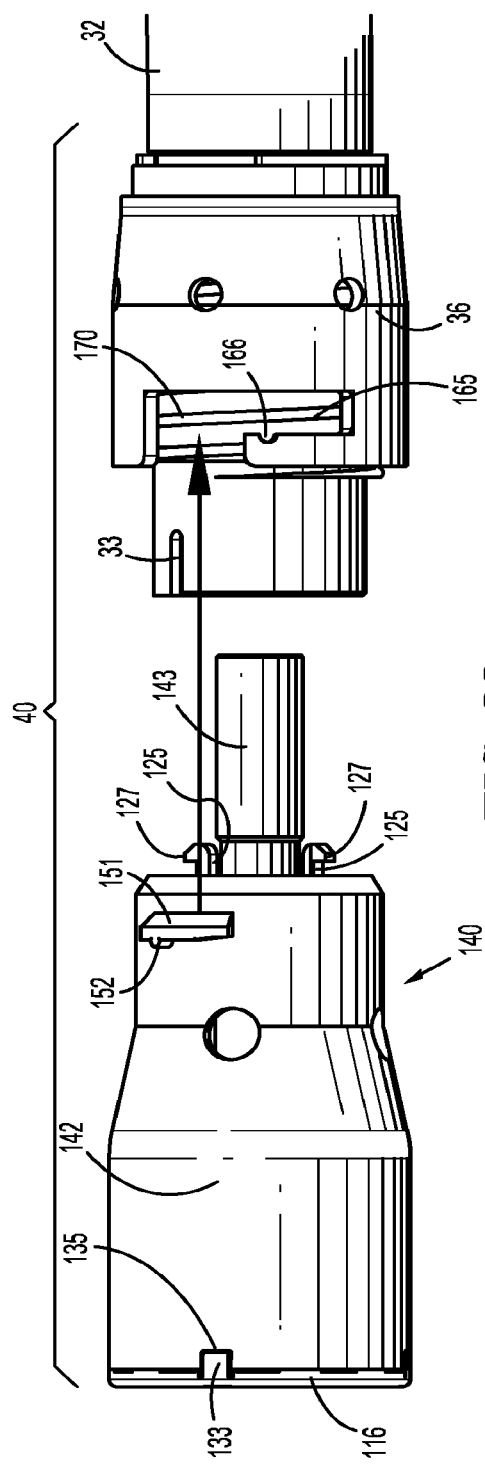
FIG. 22 is a side view of the replaceable stapling assembly and the outer tube assembly shown disengaged from one another.
Figure 23:
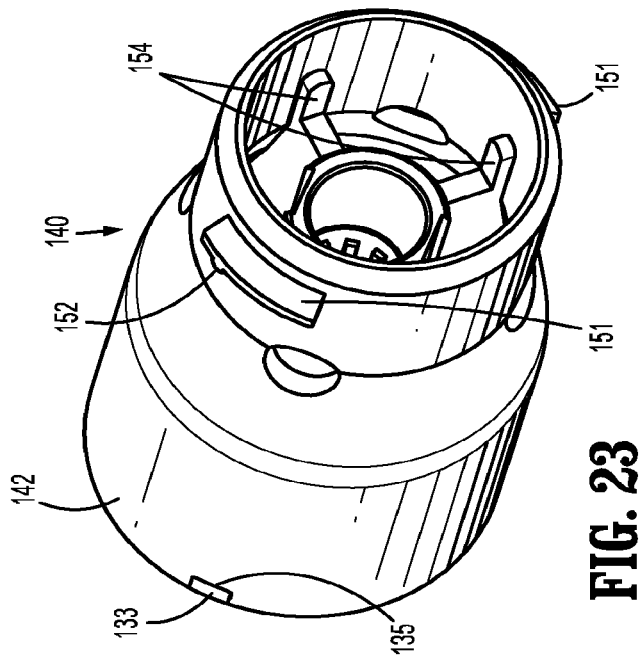
FIG. 23 is a side, perspective view from a proximal end of the replaceable stapling assembly of the surgical stapling apparatus shown in FIG. 1.
Figure 25:
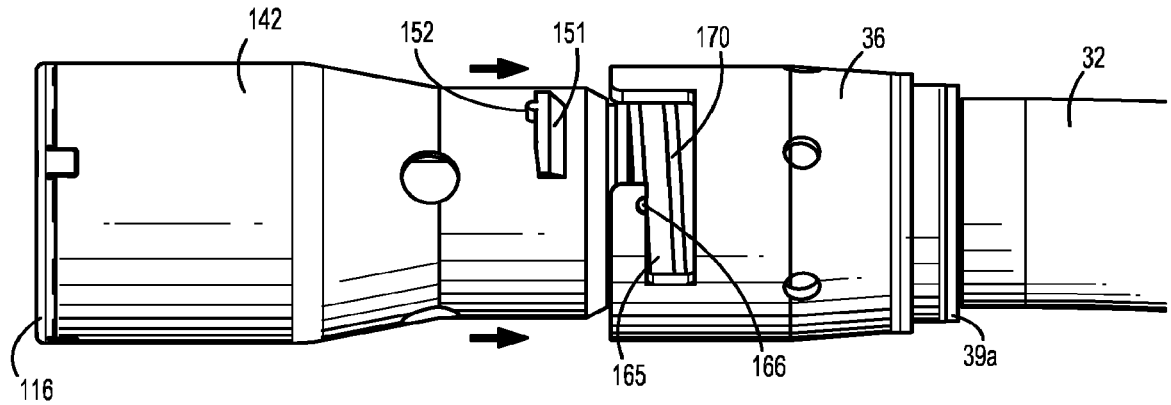
FIG. 25 is a side view of the replaceable stapling assembly during initiation of engagement between the replaceable stapling assembly and the outer tube assembly of the surgical stapling apparatus shown in FIG. 1.
Figure 26:
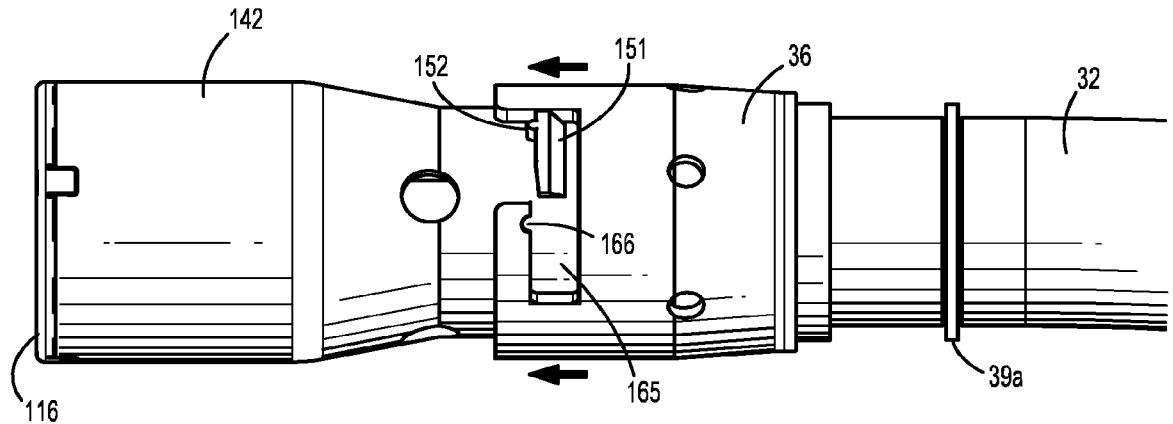
FIG. 26 is a side view of the replaceable stapling assembly during engagement between the replaceable stapling assembly and the outer tube assembly of the surgical stapling apparatus shown in FIG. 1.
Figure 27:
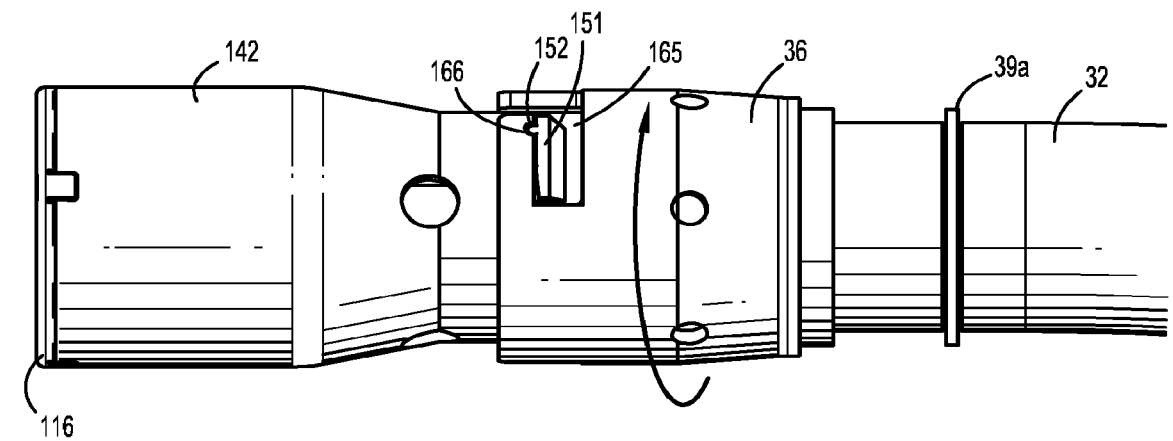
FIG. 27 is a side view of the replaceable stapling assembly shown engaged to the outer tube assembly of the surgical stapling apparatus shown in FIG. 1.
Figure 31:
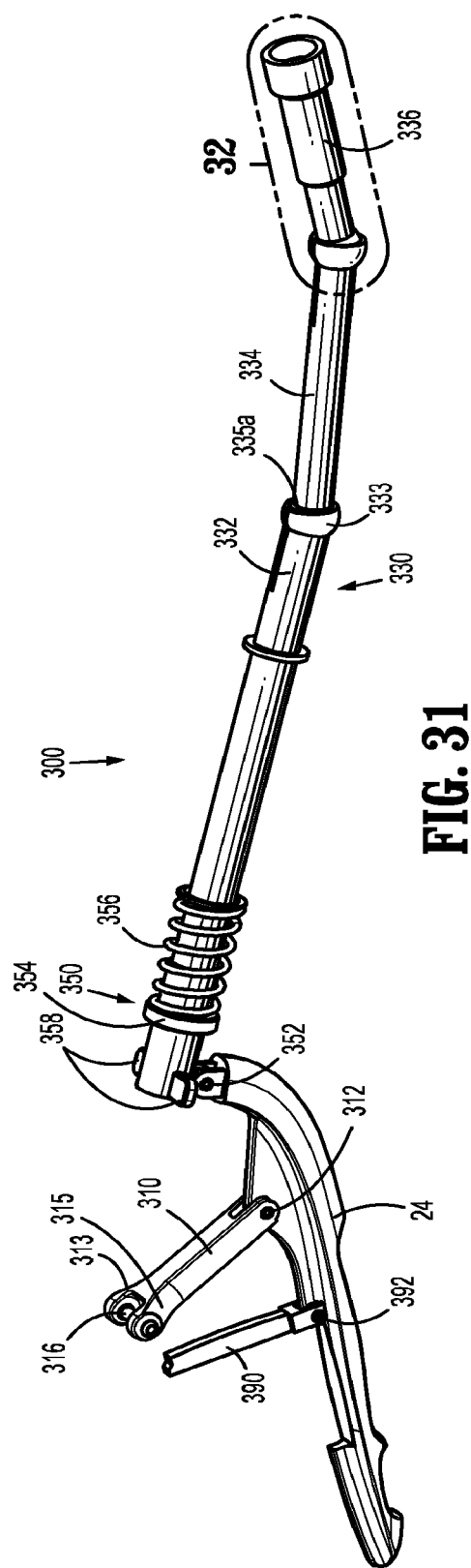
FIG. 31 is a side, perspective view of the firing assembly of the surgical stapling apparatus shown in FIG. 1.
Figure 32:
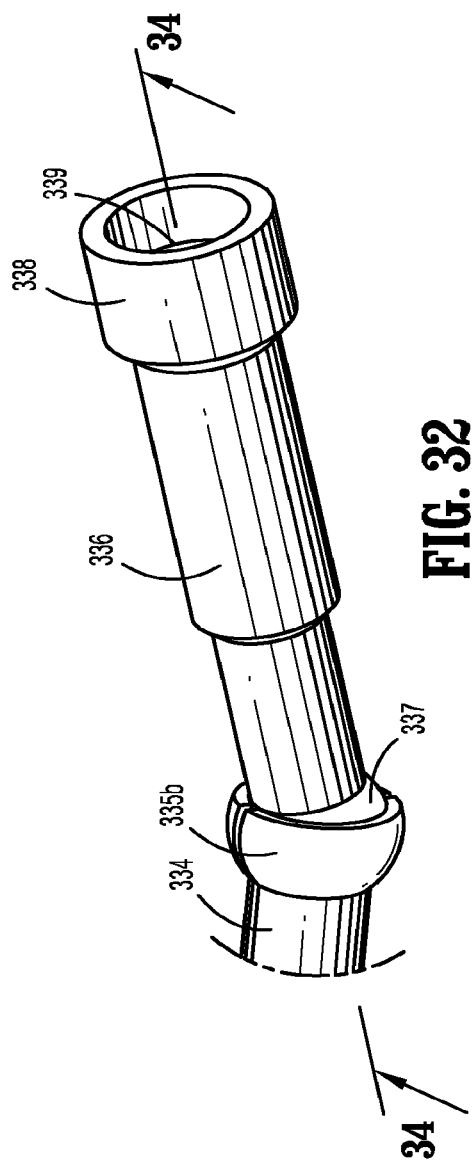
FIG. 32 is an enlarged view of the area of detail indicated as "32" in FIG. 31.
Figure 33:
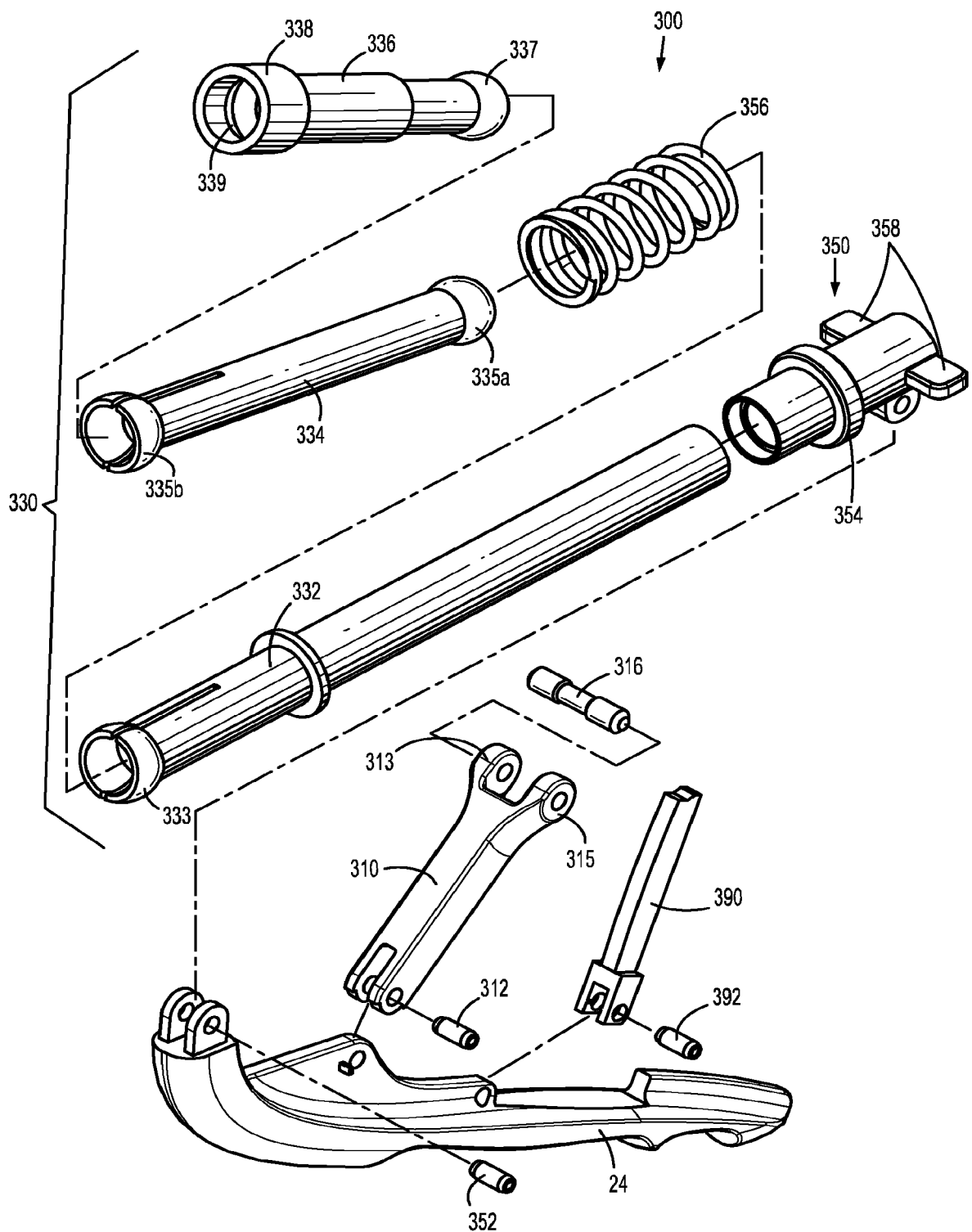
FIG. 33 is an exploded, perspective view of the firing assembly of the surgical stapling apparatus shown in FIG. 13.

Referring to FIGS. 16-18, engagement shell 36 of central elongated body portion 30 includes a distal cylindrical section 161, a central conical section 162, and a proximal cylindrical section 163 that defines a smaller diameter than distal cylindrical section 161. Engagement shell 36, outer tube 32, and/or proximal bushing 34 of central elongated body portion 30 may be formed from a sterilizable material, e.g., stainless steel or other suitable sterilizable material (metals, plastics, etc.), such that these components may be sterilized and reused without the material substantially degrading. A plurality of openings 164 are formed in conical section 162 to permit fluid and tissue passage during operation of surgical stapling apparatus 10. Proximal cylindrical section 163 of engagement shell 36 is rotatably supported about the distal end of outer tube 32 of elongated body portion 30 in any suitable fashion, e.g., via engagement between first and second C-clips 39a, 39b which are supported on the distal end of outer tube 32. With engagement shell 36 disposed about outer tube 32 between C-clips 39a, 39b, a relatively small amount of longitudinal translation of engagement shell 36 relative to outer tube 32 is permitted such that engagement shell 36 is permitted to move or slide about outer tube 32 between first C-clip 39a and second C-clip 39b as will be discussed in further detail below.

Referring also to FIGS. 22-27, distal cylindrical section 161 of engagement shell 36 is configured to receive proximal cylindrical section 149 of distal shell 142. More specifically, distal cylindrical section 161 of engagement shell 36 includes a pair of opposed engagement slots 165 configured to receive engagement tabs 151 of distal shell 142. Engagement slots 165 each define an open end configured to permit passage of engagement tabs 151 therethrough upon insertion of proximal cylindrical section 149 of distal shell 142 into distal cylindrical section 161 of engagement shell 36. Engagement slots 165 also include a transverse portion configured to permit lateral translation of a respective engagement tab 151 upon relative rotation between distal shell 142 and engagement shell 36. Slots 165 each further include an engagement notch 166 (FIG. 22) configured for receipt of a respective engagement nub 152 therein to facilitate releasable securement of stapling assembly 100 at the distal end of outer tube 32 of elongated body portion 30, as will be described below. Further, a biasing member 170 is positioned about outer tube 32 between outer tube 32 and engagement shell 36 and, more particularly, between second C-clip 39b and proximal cylindrical section 163 of engagement shell 36. Biasing member 170 is configured to bias engagement shell 36 proximally about outer tube 32.

With reference to FIGS. 14 and 17-21, cartridge assembly 110 is housed within distal shell 142 of engagement assembly 140 and includes a pusher 112, a cylindrical knife 114, and a staple guide cap 116. As mentioned above, cartridge assembly 110 and distal shell 142 are configured as disposable components. Thus, a new cartridge assembly 110 is provided when distal shell 142 is replaced after each use. Pusher 112 of cartridge assembly 110 includes a central bore 118 and is configured to be received within distal shell 142. More specifically, pusher 112 includes a distal cylindrical section 119, which is slidably positioned within distal cylindrical section 147 of distal shell 142, a central conical section 121, which is slidably positioned within central conical section 148 of distal shell 142, and a proximal cylindrical section 123 having a smaller diameter than distal cylindrical section 119, which is slidably positioned within proximal cylindrical section 149 of distal shell 142. The proximal end of pusher 112 includes a pair of proximally-extending arm members 125. Arm members 125 each include a finger 127 that is configured for insertion into and locking engagement within annular recess 339 of collar 338 of distal segment 336 of pusher link assembly 330. Thus, with pusher link assembly 330 engaged to pusher 112, actuation of firing trigger 24 urges pusher 112 distally to eject staples 600 from cartridge assembly 110 of stapling assembly 100.

The distal end of pusher 112 includes a plurality of distally-extending pusher fingers 129 dimensioned to be slidably received within slots 131 formed in staple guide cap 116. Staple guide cap 116 is supported within and engaged about the distal end of distal shell 142 via the positioning of tabs 133 within recesses 135, e.g., via snap-fit, welding, adhesion, etc. Each slot 131 formed within staple guide cap 116 is configured to retain a surgical staple 600 such that, upon advancement of pusher 112 within distal shell 142 via actuation of firing trigger 24, surgical staples 600 are ejected from slots 131 of staple guide cap 116, through tissue, and into anvil head 414 (FIGS. 47 and 49) of anvil assembly 400 (FIGS. 47 and 49) for formation about tissue.

As shown in FIGS. 14, 47 and 49, cylindrical knife 114 is pinned within bore 118 of pusher 112 to fixedly secure knife 114 in relation to pusher fingers 129 such that advancement of pusher 112 to eject surgical staples 600 from staple guide 116 is effected simultaneously with advancement of knife 114 through tissue. The distal end of knife 114 includes a circular cutting edge 115 to facilitate the cutting of tissue.

Figure 36:
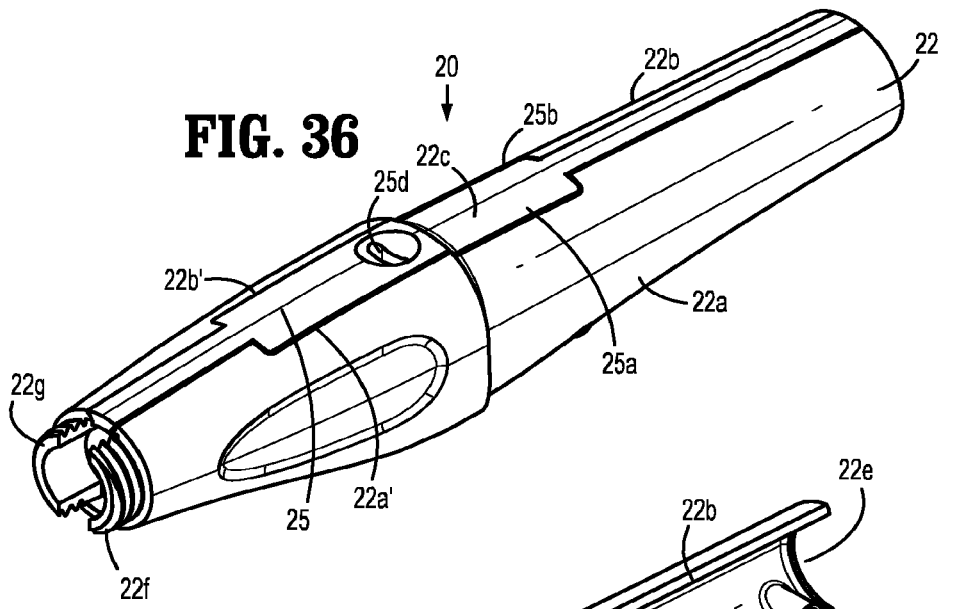
FIG. 36 is a top, side, perspective view from a distal end of the stationary handle of the handle assembly of the surgical stapling apparatus shown in FIG. 1.
Figure 37:
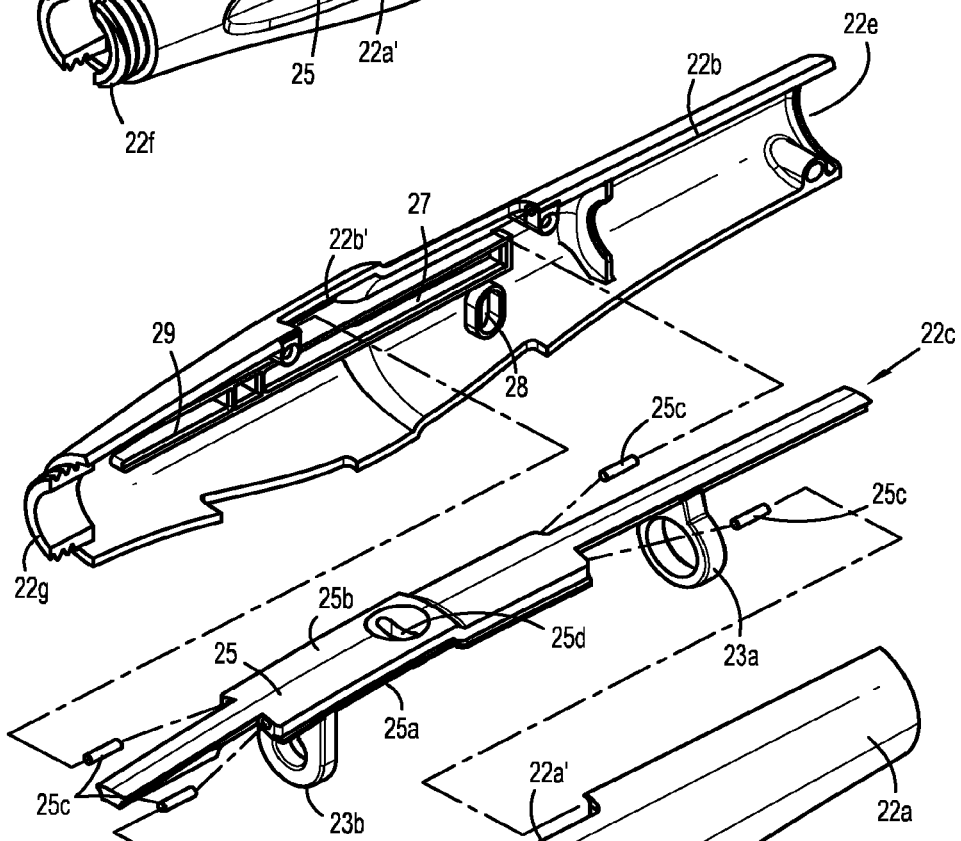
FIG. 37 is an exploded, side, perspective view of the stationary handle of the surgical stapling apparatus shown in FIG. 36.
Figure 38:
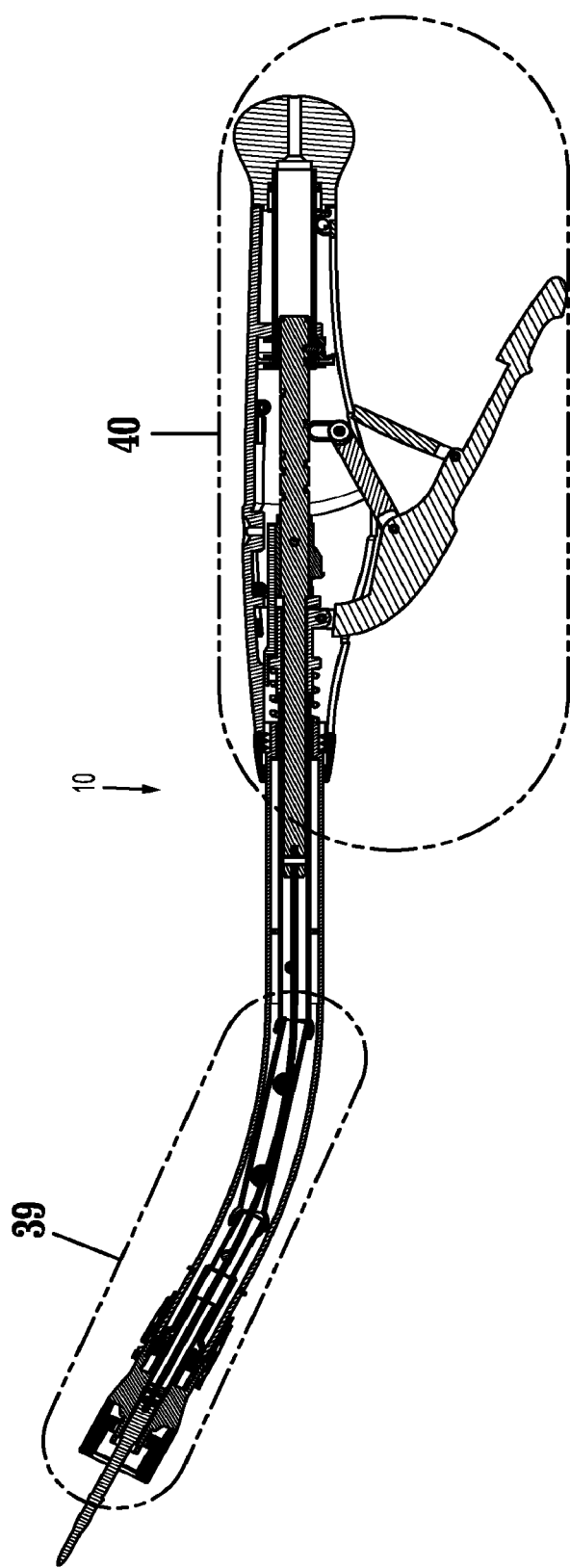
FIG. 38 is a longitudinal, cross-sectional view of the surgical stapling apparatus shown in FIG. 1 with the anvil assembly removed.
Figure 39:
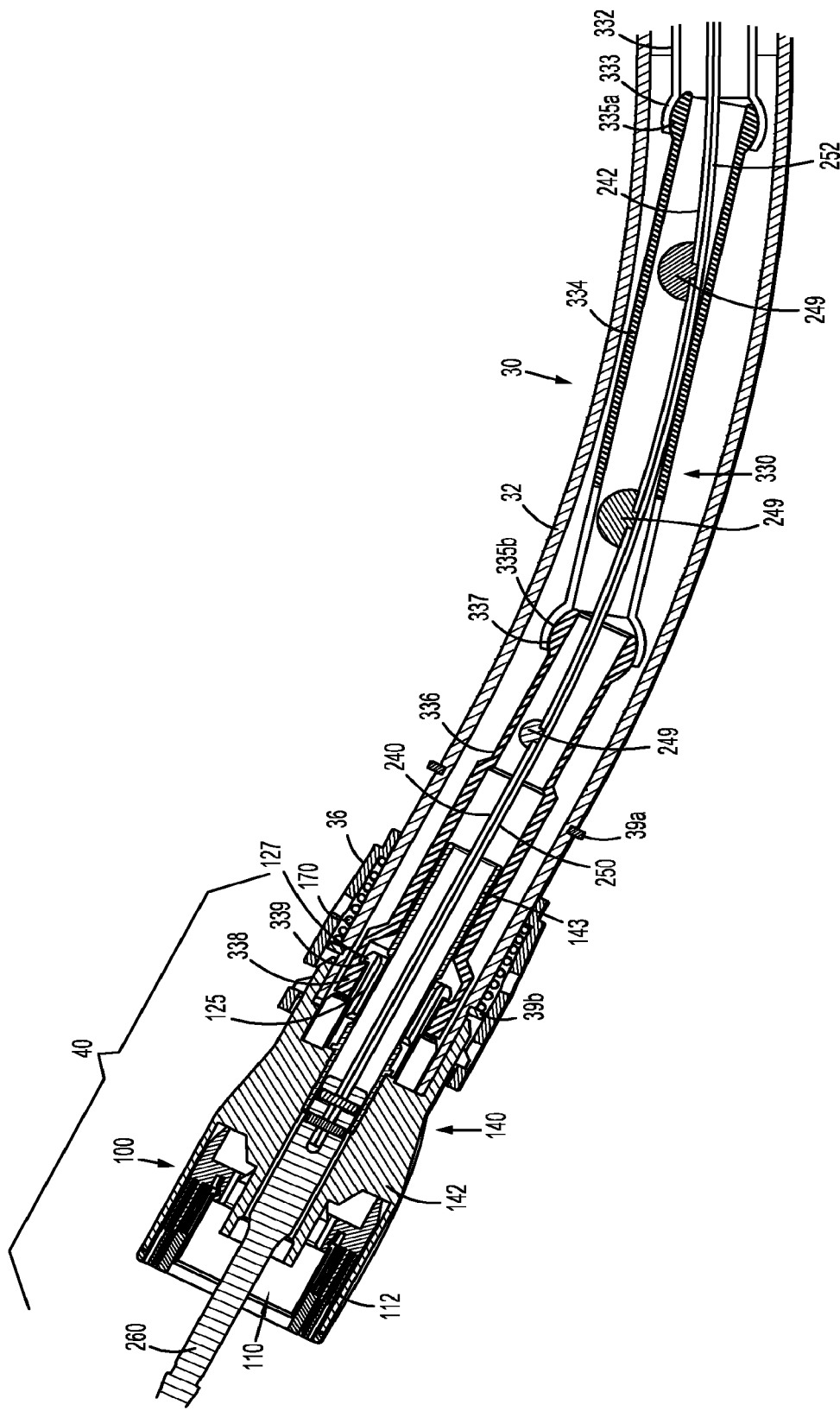
FIG. 39 is an enlarged view of the area of detail indicated as "39" in FIG. 38.

With reference to FIGS. 36 and 37, as mentioned above, stationary handle 22 is formed from first and second handle sections 22a, 22b and support chassis 22c that cooperate to house and support the internal components of handle portion 20. Handle sections 22a, 22b and support chassis 22c are configured as reusable, sterilizable components, although handle sections 22a, 22b and/or chassis 22c may alternatively be configured as disposable components.

Support chassis 22c includes a central body portion 25 having first and second lateral flanges 25a, 25b that are configured for receipt and pivotable engagement within first and second recesses 22a', 22b' of handle sections 22a, 22b, respectively. Engagement pins 25c are provided at the proximal and distal ends of lateral flanges 25a, 25b and are configured for pivotable engagement within corresponding apertures defined within handle sections 22a, 22b adjacent recesses 22a', 22b'. Pins 25c pivotably secure handle sections 22a and 22b to flanges 25a, 25b of support chassis 22c within recesses 22a', 22b'. Pins 25c may be configured for snap-fit engagement within the apertures of handle sections 22a, 22b, although other pivotable securement mechanisms are also contemplated.

Central body portion 25 of support chassis 22c further includes an indicator window 25d through which visual indicators 278a, 278b may be viewed, and proximal and distal support rings 23a, 23b, respectively, for supporting collar 232 and screw 220, respectively, of approximation assembly 200. Indicator window 25b may be formed via a hole or aperture extending through central body portion 25 of support chassis 22c or may be formed from a transparent section of central body portion 25.

Handle sections 22a, 22b further include threaded distal extensions 22f, 22g that cooperate to define a generally annular threaded member for releasably engaging proximal bushing 34 of central body portion 30. Engagement between distal extensions 22f, 22g and proximal bushing 34 releasably secures outer tube 32 and handle portion 20 to one another and also secures handle sections 22a, 22b to one another at the distal ends thereof. A pin (not shown) extending from handle section 22a is configured for frictional receipt within an aperture 22d of handle section 22b to releasably secure handle sections 22a, 22b to one another at the proximal ends thereof. The securement of handle sections 22a, 22b to one another retains support chassis 22c in a fixed position relative to handle sections 22a, 22b, e.g., with handle sections 22a, 22b secured to one another, support chassis 22c is no longer permitted to pivot relative to handle sections 22a, 22b.

Figure 40:
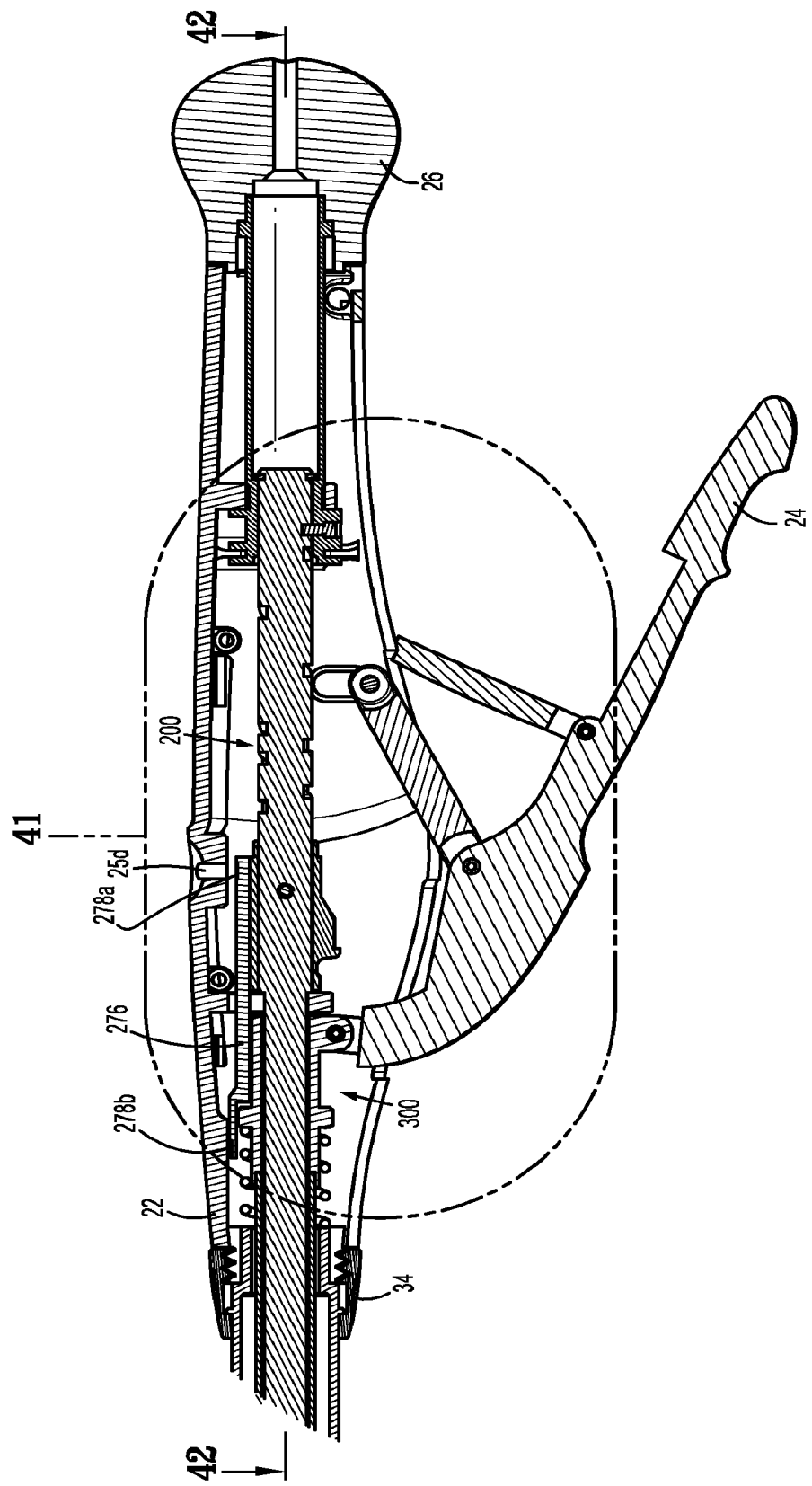
FIG. 40 is an enlarged view of the area of detail indicated as "40" in FIG. 38.
Figure 41:
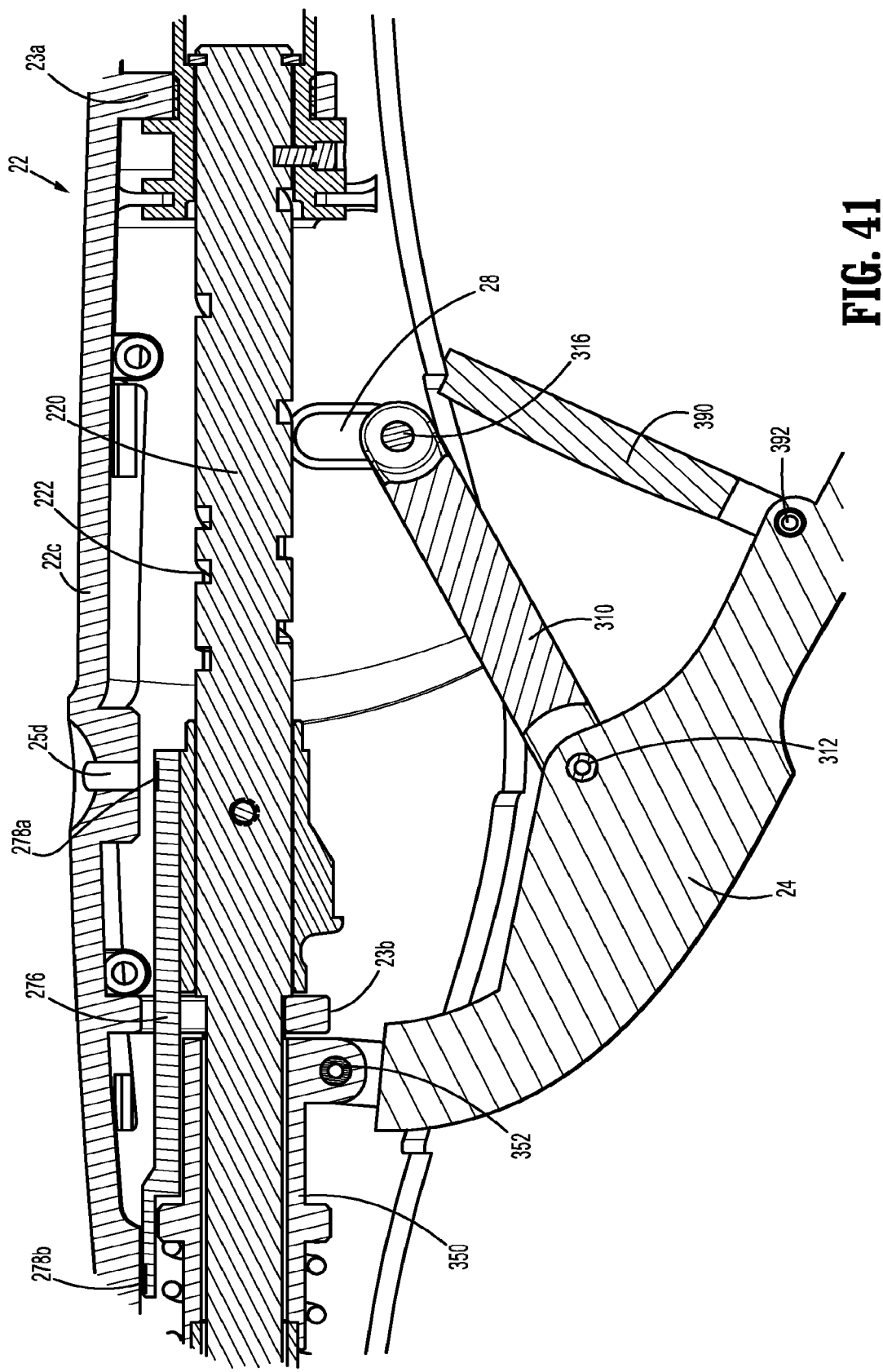
FIG. 41 is an enlarged, cross-sectional view of the area of detail indicated as "41" in FIG. 40.
Figure 42:
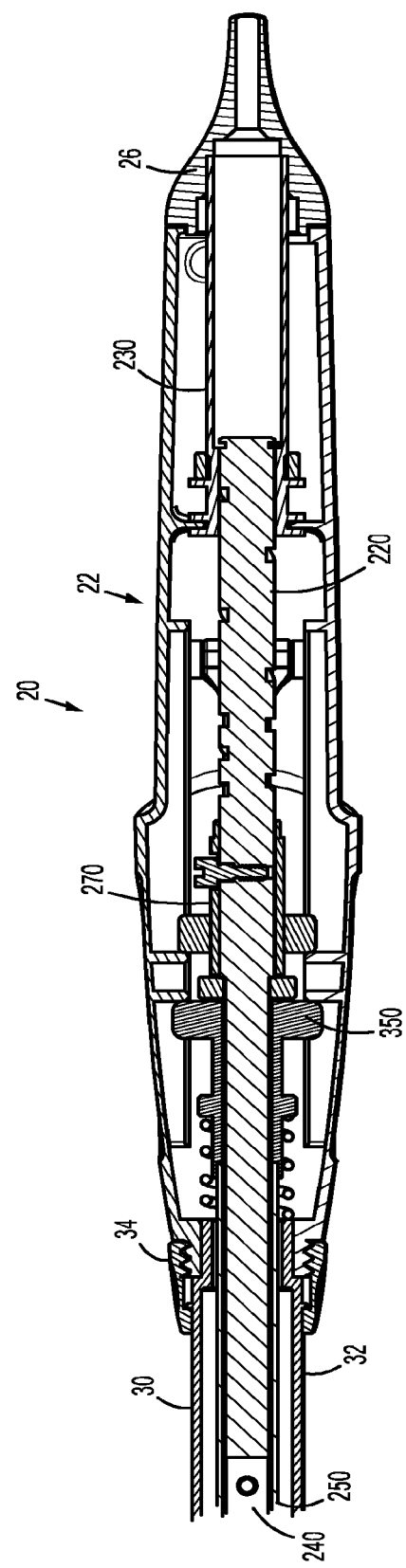
FIG. 42 is a longitudinal, cross-sectional view taken along section line 42-42 of FIG. 40.

The use of surgical stapling apparatus 10, disassembly of surgical stapling apparatus 10 for sterilization of the reusable components and replacement of the disposable components, and reassembly of surgical stapling apparatus 10 for subsequent use is now described in detail. With reference to FIGS. 38-49, in use, distal head portion 40 (FIG. 1) of surgical stapling apparatus 10 (FIG. 38) inserted into an internal surgical site, before after engagement of anvil assembly 400. Next, anvil assembly 400 and stapling assembly 100 are positioned adjacent tissue to be stapled. At this point, as shown in FIGS. 40 and 41, safety bar 390 is disposed in the safety position such that actuation of firing trigger 24 is inhibited. Once distal head portion 40 (FIG. 1) of surgical stapling apparatus 10 is positioned as desired, anvil assembly 400 may be approximated relative to stapling assembly 100 to clamp tissue therebetween via manipulating approximation assembly 200. More specifically, anvil assembly 400 is moved to the approximated or closed position to grasp tissue between anvil assembly 400 and stapling assembly 100 by rotating rotation knob 26 in a first direction (FIG. 43). Rotation of knob 26 in the first direction causes cylindrical sleeve 230 to rotate to move pin 224 along helical channel 222 of screw 220 such that screw 220 is translated proximally (FIG. 44). The distal end of screw 220 is connected to screw extensions 240 and 250 which, in turn, are fastened at their distal ends to anvil retainer 260, such that anvil retainer 260 is likewise translated proximally to approximate anvil assembly 400 relative to stapling assembly 100. Knob 26 may be rotated to approximate anvil assembly 400 relative to stapling assembly 100 to clamp tissue therebetween until the minimum tissue gap between anvil assembly 400 and stapling assembly 100 (FIG. 47), which is set via screw stop 270, is achieved. As screw 220 is translated proximally, screw stop 270, which is supported on screw 220, is moved proximally. Movement of the anvil assembly 400 to the approximated position can be confirmed once visual indicator 278b is viewable through indicator window 25d of central body portion 25 of support chassis 22c (see FIGS. 44-46).

Figure 48:
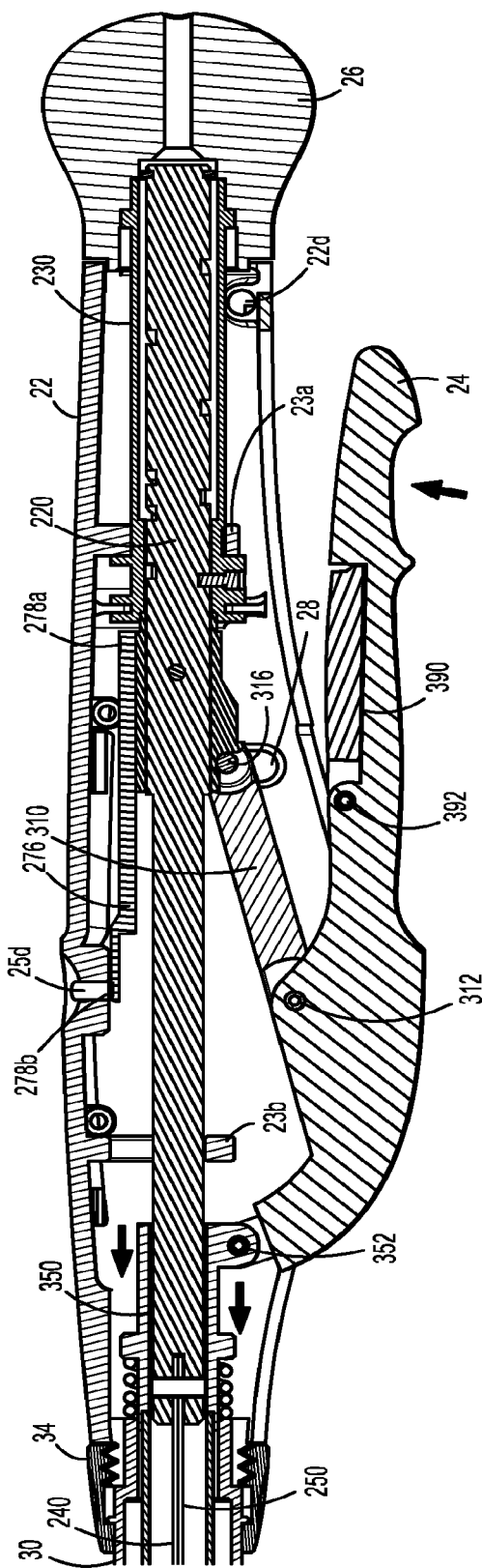
FIG. 48 is a longitudinal, cross-sectional view of the handle portion of the surgical stapling apparatus of FIG. 1 shown in a position corresponding to the fired position of the surgical stapling apparatus.

Referring also to FIG. 14, with anvil assembly 400 disposed in the approximated position clamping tissue between anvil head 414 and staple guide cap 116 of stapling assembly 100 (as shown in FIG. 47), firing assembly 300 may be actuated to staple and core the clamped tissue. First, in order to allow for firing, safety bar 390 is rotated from the safety position (FIGS. 40 and 41) to the ready position (FIG. 43). With safety bar 390 no longer inhibiting actuation of firing trigger 24, firing assembly 400 may be actuated. In order to fire surgical stapling apparatus 10, trigger 24 is compressed towards stationary handle 22, as shown in FIG. 48. As described above, the distal end of firing trigger 24 is connected through coupling member 350 to the proximal end of pusher link assembly 330. Accordingly, as firing trigger 24 is actuated, pusher link assembly 330 is moved distally to urge pusher 112 of cartridge assembly 110 distally. Upon distal translation of pusher 112 relative to staple guide cap 116, fingers 129 of pusher 112 engage and eject staples 600 from staple guide cap 116, through tissue, and into anvil head 414 of anvil assembly 400, which form staples 600 about tissue (FIG. 49). Cylindrical knife 114 is moved concurrently with pusher 112 such that knife 114 is likewise advanced distally to core tissue.

In one exemplary method of use, surgical stapling apparatus 10 is used to perform a circular anastomosis. Typically, circular anastomoses are required during procedures for removing a portion of a diseased vessel such as the colon or the intestine. During such a procedure, the diseased portion of the vessel is removed and the end portions of the remaining first and second vessel sections are joined together using the surgical stapling apparatus 10.

During such a procedure using the surgical stapling apparatus 10, prior to removing the diseased vessel portion from the diseased vessel, the anvil assembly 400 with a removable trocar (not shown) attached thereto is positioned in the first vessel section on a first side of the diseased portion. A removable trocar which is suitable for use with the anvil assembly 400 is disclosed in U.S. Pat. No. 6,945,444 to Gresham et al., which, as discussed above, is incorporated herein by reference in its entirety. After the diseased vessel portion is removed and the open ends of the first and second vessel sections have been sutured, the distal end of apparatus 10 is positioned in the second vessel section on the other side of the diseased vessel portion which has been removed. At this time, the removable trocar is pushed through the suture line in the end of the first vessel section and removed from the anvil assembly. Next, trocar tip 267 of anvil retainer 260 is pushed through the suture line in the second vessel section and is joined to the center rod of the anvil assembly 400. The surgical stapling apparatus 10 can now be approximated and fired in the manner discussed above to join the ends of the first and second vessel sections and core out any tissue obstructing the vessel lumen.

At the completion of the stapling operation, surgical stapling apparatus 10 may be removed from the internal surgical site. More specifically, anvil assembly 400 may be configured to pivot to a low-profile configuration after firing and upon un-approximation of anvil assembly 400 relative to stapling assembly 100 to facilitate removal of surgical stapling apparatus 10 from the internal surgical site. A suitable tilting mechanism is described in U.S. Pat. No. 7,857,187 to Milliman or U.S. Pat. No. 6,945,444 to Gresham et al., previously incorporated by reference herein in their entirety. Alternatively, anvil assembly 400 need not have a pivotal head and may be removed from the surgical site in the same orientation as it was advanced into the surgical site.

Upon removal from the internal surgical site at the completion of the surgical procedure, surgical stapling apparatus 10 may be disassembled to facilitate sterilization of the reusable components and replacement of the disposable components. More specifically, and with reference to FIGS. 13-37, to disassemble surgical stapling apparatus 10, anvil assembly 400 (FIGS. 1, 47, and 49) is first removed from anvil retainer 260. In order to disengage anvil assembly 400 from anvil retainer 260, anvil assembly 400 is moved to an unapproximated position spaced-apart from stapling assembly 100 by rotating knob 26 in a second, opposite direction, sufficiently such that annular protrusion 268 of anvil retainer 260 and annular recess 426 of anvil center rod 422 are no longer positioned within inner guide portion 146 of stapling assembly 100. Once anvil assembly 400 has been unapproximated, anvil assembly 400 may be separated from anvil retainer 260 by applying sufficient force to the anvil assembly 400 so as to flex center rod 422 radially outwardly to disengage annular protrusion 268 from annular recess 426, thus allowing anvil assembly 400 to be removed from anvil retainer 260. Anvil assembly 400 is configured as a sterilizable, reusable component although it is also contemplated that anvil assembly be configured as a reusable component.

Once anvil assembly 400 (FIGS. 1, 47, and 49) has been removed, stapling assembly 100 may be disengaged from surgical stapling apparatus 10. More specifically, stapling assembly 100 is disengaged from the distal end of outer tube 32 by first urging engagement shell 36 distally against the bias of biasing member 170 and relative to proximal shell 142 such that engagement nubs 152 of distal shell 142 are disengaged from engagement notches 166 of engagement shell 36. Thereafter, engagement shell 36 is rotated relative to distal shell 142 such that engagement tabs 151 are translated along the transverse portions of engagement slots 165 to the open ends thereof. Once sufficiently rotated such that engagement tabs 151 are aligned with the open ends of engagement slots 165, proximal section 149 of distal shell 142 is squeezed inwardly and translated distally to disengage fingers 127 of arms 125 of cartridge assembly 110 from engagement within annular recess 339 of collar 338 of distal segment 336 of pusher link assembly 330. Thereafter, engagement shell 36 is allowed to return proximally under the bias of biasing member 170 such that engagement tabs 151 are released from engagement slots 165, thereby disengaging distal shell 142 from engagement shell 36.

Once disengaged, stapling assembly 100 may then be removed from positioning about anvil retainer 260 and may be disposed of, although it is also contemplated that one or more components of stapling assembly 100 be sterilizable for reuse.

In order to disassemble handle portion 22 in preparation for sterilization, proximal bushing 34 is disengaged from the distal ends of handle sections 22a, 22b by rotating proximal bushing 34 relative to handle portion 22. Next, the lower ends of handle sections 22a, 22b are pivoted away from one another and relative to support chassis 22c to open handle portion 22, thus exposing approximation assembly 200 and firing assembly 300.

Once handle sections 22a, 22b have been pivoted relative to support chassis 22c to open handle portion 22, approximation assembly 200 and firing assembly 300 may be removed from support chassis 22c and handle portion 22. Thus, with handle portion 22 opened, and with approximation assembly 200 and firing assembly 300 removed from handle portion, sterilization of each of these components for reuse may be readily achieved. Alternatively, one or more of theses components may be configured as a disposable component and, thus, may be replaced with a new component rather than being sterilized.

Once the reusable components, e.g., handle sections 22a, 22b, support chassis 22c, approximation assembly 200, and firing assembly 300, have been sterilized and the replaceable components, e.g., stapling assembly 100, replaced, surgical stapling apparatus 10 may be reassembled for subsequent use. Initially, the distal end of approximation assembly 200 is inserted through coupling member 350 and pusher link assembly 330 of firing assembly 300. Next, approximation assembly 200, with firing assembly 300 disposed therein, is mounted within support rings 23a, 23b, of support chassis 22c such that a wing 274 of screw stop 270 is slidably received within channel 27 of handle section 22b, a wing 358 of coupling member 350 is slidably received within channel 29 of handle section 22b (see FIGS. 8-9), and pivot member 316 is received within vertical slot 28 of handle section 22b. Once approximation assembly 200 and firing assembly 300 are mounted on support chassis 22c, handle sections 22a, 22b may be closed, or pivoted towards one another and relative to support chassis 22c to house the proximal components of firing assembly 300 and approximation assembly 200 therein.

Next, elongated central body portion 30 may be maneuvered into position such that outer tube 32 is disposed about pusher link assembly 330 of firing assembly 300, which is disposed about screw extensions 240, 250 of approximation assembly 200, with anvil retainer 260 extending distally from both pusher link 330 and outer tube 32. The proximal end of outer tube 32 may be secured relative to stationary handle 22 via threadingly engaging proximal bushing 34 about distal extensions 22f, 22g of handle sections 22a, 22b, respectively.

With reference to FIGS. 17-27, in order to assemble stapling assembly 100 and anvil assembly 400 at the distal end of outer tube 32, cartridge assembly 110, which is engaged within distal shell 142, is approximated relative to the engagement shell 36 disposed at the distal end of outer tube 32. More specifically, distal shell 142, including cartridge assembly 110, is positioned about anvil retainer 260 and is approximated relative to the distal end of outer tube 32 such that orientation bars 154 of distal shell 142 are received within slots 33 defined at the distal end of outer tube 32 to ensure proper alignment therebetween. Upon further advancement of cartridge assembly 110 and distal shell 142 towards the distal end of outer tube 32, fingers 127 of proximally-extending arm members 125 of pusher 112 of cartridge assembly 110 are inserted into distal segment 336 of pusher link assembly 330 and are engaged within annular recess 339 defined therein to engage cartridge assembly 110 and pusher link assembly 330 to one another.

With cartridge assembly 110 engaged at the distal end of pusher link assembly 330, engagement shell 36 is moved distally against the bias of biasing member 170 such that engagement tabs 151 of distal shell 142 are inserted through the open ends of engagement slots 165 of engagement shell 36. Once engagement tabs 151 of distal shell 142 are inserted into engagement slots 165 of engagement shell 36, engagement shell 36 is rotated relative to distal shell 142 such that engagement tabs 151 are translated along the transverse portions of engagement slots 165 and away from the open ends thereof. Once sufficiently rotated to the position shown in FIG. 27, engagement shell 36 may be released, allowing biasing member 170 to bias engagement shell 36 proximally and away from distal shell 142 such that engagement nubs 152 are received within engagement notches 166 to secure distal shell 142 and engagement shell 36 to one another about the distal end of outer tube 32.

With reference to FIGS. 1, 47, and 49, once stapling assembly 100 is engaged about the distal end of outer tube 32, anvil assembly 400 may be engaged to anvil retainer 260, which extends distally through and from stapling assembly 100. In order to engage anvil assembly 400 about anvil retainer 260, anvil center rod 422 is disposed about anvil retainer 260 until annular recess 426 receives annular protrusion 268 of anvil retainer 260 to secure anvil assembly 400 about anvil retainer 260. Upon retraction of anvil retainer 260 during movement of anvil assembly 400 to the approximated position to clamp tissue between stapling assembly 100 and anvil assembly 400, annular protrusion 268 is positioned within stapling assembly 100, thus inhibiting removal of anvil assembly 400 therefrom due to the inability of annular recess 426 of anvil center rod 422 to flex outwardly to disengage from annular protrusion 268. Rather, removal of anvil assembly 422 is only permitted when anvil retainer 260 is disposed in an extended position, e.g., the position shown in FIG. 1.

As can be appreciated, the above-described cycle of use, disassembly, sterilization and replacement, and reassembly, may be repeated for a plurality of usage cycles.

It will be understood that various modifications may be made to the embodiments of the surgical stapling apparatus disclosed herein. Therefore, the above description should not be construed as limiting, but merely as exemplifications of embodiments. Those skilled in the art will envision other modifications within the scope and spirit of the present disclosure.

What is claimed is:
1. A surgical stapling apparatus, comprising:
  a handle portion;
  an elongated body portion extending distally from the handle portion, the elongated body portion defining a curved configuration;
  a firing assembly including a firing trigger, a firing link, and a pusher link extending through the elongated body portion, the pusher link being movably supported for distal translation through the elongated body portion in response to actuation of the firing trigger, the pusher link including a plurality of straight segments pivotably coupled to one another via ball-and-socket joints to enable translation of the straight segments through the curved configuration of the elongated body portion, the plurality of straight segments and the ball and socket joints being hollow and defining a channel through the pusher link;
an approximation assembly including a drive member and extending through the channel of the pusher link, the drive member configured to engage an anvil assembly; and
a stapling assembly including a staple guide cap that supports a plurality of surgical staples and a pusher that is engaged with the pusher link, the stapling assembly secured at a distal end of the elongated body portion, wherein distal advancement of the pusher link advances the pusher in relation to the staple guide cap to eject the plurality of surgical staples from the stapling assembly.

2. The surgical stapling apparatus according to claim 1, wherein the plurality of straight segments include a proximal straight segment, an intermediate straight segment, and a distal straight segment, the proximal and intermediate straight segments coupled to one another via a first ball and socket joint and the intermediate and distal straight segments coupled to one another via a second ball and socket joint.

3. The surgical stapling apparatus according to claim 1, wherein the drive member includes at least one flexible band extending at least partially through the plurality of straight segments and the ball and socket joints.

4. The surgical stapling apparatus according to claim 3, wherein at least one spacer extends from the at least one flexible band, each spacer configured to contact an interior surface of at least one of the straight segments to maintain alignment and guide translation of the drive member through the plurality of straight segments.

5. The surgical stapling apparatus according to claim 1, further comprising an approximation knob extending from the handle portion, the approximation knob coupled to the drive member and selectively actuatable to move the anvil assembly between a spaced-apart position and an approximated position relative to the stapling assembly.

6. The surgical stapling apparatus according to claim 5, wherein the drive member defines a helical channel and wherein the approximation knob is coupled to a pin disposed within the helical channel such that rotation of the approximation knob effects translation of the drive member.

7. The surgical stapling apparatus according to claim 1, wherein the stapling assembly is releasably secured at the distal end of the elongated body portion.

8. The surgical stapling apparatus according to claim 1, wherein the stapling assembly includes a cartridge assembly disposed within the outer shell.

9. A surgical stapling apparatus, comprising:
a handle portion;
an elongated body portion extending distally from the handle portion;
a firing assembly including a firing trigger, a firing link, and a pusher link extending through the elongated body portion, the pusher link being movably supported for distal translation through the elongated body portion in response to actuation of the firing trigger, the pusher link including a plurality of segments coupled to one another via ball-and-socket joints, the plurality of segments and the ball-and-socket joints being hollow and defining a channel through the pusher link;
an approximation assembly, the approximation assembly including a drive member and extending through the channel of the pusher link distally from the elongated body portion, the distal end of the drive member configured to engage an anvil assembly; and
a stapling assembly including a staple guide cap that supports a plurality of surgical staples and a pusher that is engaged with the pusher link, the stapling assembly secured at a distal end of the elongated body portion, wherein distal advancement of the pusher link advances the pusher in relation to the staple guide cap to eject the plurality of surgical staples from the stapling assembly towards the anvil assembly.

10. The surgical stapling apparatus according to claim 9, wherein the plurality of segments include a proximal segment, an intermediate segment, and a distal segment, the proximal and intermediate segments coupled to one another via a first ball and socket joint and the intermediate and distal segments coupled to one another via a second ball and socket joint.

11. The surgical stapling apparatus according to claim 9, wherein the drive member includes at least one flexible band extending through the plurality of segments and the ball and socket joints.

12. The surgical stapling apparatus according to claim 11, wherein at least one spacer extends from the at least one flexible band, each spacer configured to contact an interior surface of at least one of the segments to maintain alignment and guide translation of the drive member through the plurality of segments.

13. The surgical stapling apparatus according to claim 9, further comprising an approximation knob extending from the handle portion, the approximation knob coupled to the drive member and selectively actuatable to move the anvil assembly between a spaced-apart position and an approximated position relative to the stapling assembly.

14. The surgical stapling apparatus according to claim 13, wherein the drive member defines a helical channel and wherein the approximation knob is coupled to a pin disposed within the helical channel such that rotation of the approximation knob effects translation of the drive member.

15. The surgical stapling apparatus according to claim 9, wherein the stapling assembly is releasably secured at the distal end of the elongated body portion.

16. The surgical stapling apparatus according to claim 9, wherein the stapling assembly includes a cartridge assembly disposed within the outer shell.

17. The surgical stapling apparatus according to claim 9, wherein the elongated body portion defines a curved configuration.

* * * * *